US009618129B2

(12) United States Patent
Block, III et al.

(10) Patent No.: US 9,618,129 B2
(45) Date of Patent: Apr. 11, 2017

(54) NORMALLY CLOSED MICROVALVE AND APPLICATIONS OF THE SAME

(71) Applicant: Vanderbilt University, Nashville, TN (US)

(72) Inventors: Frank E. Block, III, Nashville, TN (US); Philip C. Samson, Nashville, TN (US); John P. Wikswo, Brentwood, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 14/651,174

(22) PCT Filed: Nov. 21, 2013

(86) PCT No.: PCT/US2013/071324
§ 371 (c)(1),
(2) Date: Jun. 10, 2015

(87) PCT Pub. No.: WO2014/123600
PCT Pub. Date: Aug. 14, 2014

(65) Prior Publication Data
US 2015/0308578 A1    Oct. 29, 2015

Related U.S. Application Data

(63) Continuation-in-part of application No. PCT/US2013/071026, filed on Nov. 20, 2013, and a
(Continued)

(51) Int. Cl.
*F16K 11/16*      (2006.01)
*F04B 43/12*     (2006.01)
(Continued)

(52) U.S. Cl.
CPC ........ *F16K 11/163* (2013.01); *B01L 3/50273* (2013.01); *C12M 21/08* (2013.01);
(Continued)

(58) Field of Classification Search
CPC .... F16K 11/163; F04B 43/12; F04B 43/1269; F04B 43/1292; C12M 21/08;
(Continued)

(56) References Cited

U.S. PATENT DOCUMENTS 2,722,893 A * 11/1955 Maillot ................ F04B 43/021
                                                              417/474
2,920,578 A *  1/1960 Schaurte ................ F04B 43/14
                                                              417/477.7
(Continued)

FOREIGN PATENT DOCUMENTS

WO          0191831 A1    12/2001
WO     2012048261 A1     4/2012

OTHER PUBLICATIONS

Korean Intellectual Property Office, "International Search Report for PCT/US2013/071324", KR, Sep. 1, 2014.

*Primary Examiner* — Craig Schneider
*Assistant Examiner* — Kevin Barss
(74) *Attorney, Agent, or Firm* — Locke Lord LLP; Tim Tingkang Xia, Esq.

(57) ABSTRACT

A normally closed valve includes a plurality of fluid channels in fluid communication with each other, defined in a flexible base such that when a fluid channel is compressed, a fluid flow through the fluid channel is occluded, otherwise, the fluid flow through the fluid channel is unoccluded; and means for selectively compressing or uncompressing a desired fluid channel.

42 Claims, 27 Drawing Sheets

Related U.S. Application Data continuation-in-part of application No. PCT/US2012/068771, filed on Dec. 10, 2012, and a continuation of application No. 13/877,925, filed as application No. PCT/US2011/055432 on Oct. 7, 2011.

(60) Provisional application No. 61/808,455, filed on Apr. 4, 2013, provisional application No. 61/822,081, filed on May 10, 2013, provisional application No. 61/729,149, filed on Nov. 21, 2012, provisional application No. 61/569,145, filed on Dec. 9, 2011, provisional application No. 61/697,204, filed on Sep. 5, 2012, provisional application No. 61/717,441, filed on Oct. 23, 2012, provisional application No. 61/390,982, filed on Oct. 7, 2010.

(51) Int. Cl.
| | | |
|---|---|---|
| *B01L 3/00* | (2006.01) | |
| *C12M 3/00* | (2006.01) | |
| *C12M 3/06* | (2006.01) | |
| *C12M 1/00* | (2006.01) | |

(52) U.S. Cl.
CPC ............ *C12M 23/16* (2013.01); *C12M 23/44* (2013.01); *C12M 23/52* (2013.01); *C12M 29/00* (2013.01); *C12M 29/10* (2013.01); *C12M 29/20* (2013.01); *F04B 43/12* (2013.01); *F04B 43/1269* (2013.01); *F04B 43/1292* (2013.01); *B01L 2200/028* (2013.01); *B01L 2200/0684* (2013.01); *B01L 2200/10* (2013.01); *B01L 2200/18* (2013.01); *B01L 2300/0819* (2013.01); *B01L 2300/0867* (2013.01); *B01L 2300/123* (2013.01); *B01L 2400/0644* (2013.01)

(58) Field of Classification Search
CPC ...... C12M 23/16; C12M 23/44; C12M 23/52; C12M 29/00; C12M 29/20; Y10T 137/86533; B01L 3/50273
See application file for complete search history.

(56) References Cited

U.S. PATENT DOCUMENTS

| | | | | |
|---|---|---|---|---|
| 5,496,009 | A * | 3/1996 | Farrell ..................... | F15C 3/04 251/25 |
| 5,533,886 | A * | 7/1996 | Von Der Heyde .. | F04B 43/1207 417/413.1 |
| 5,840,069 | A * | 11/1998 | Robinson ............ | F04B 43/1269 417/477.3 |
| 6,296,460 | B1 | 10/2001 | Smith et al. | |
| 6,872,056 | B2 * | 3/2005 | Stiefel ................... | F04B 49/126 123/500 |
| 2002/0155010 | A1 * | 10/2002 | Karp ................. | B01L 3/502738 417/413.2 |
| 2002/0197167 | A1 * | 12/2002 | Kornelsen ............ | F04B 43/043 417/53 |
| 2006/0027772 | A1 | 2/2006 | Richter et al. | |
| 2008/0131300 | A1 * | 6/2008 | Junod ................. | F04B 43/1269 417/476 |
| 2008/0135114 | A1 * | 6/2008 | Takayama ......... | B01L 3/502738 137/561 R |
| 2008/0163946 | A1 * | 7/2008 | Gomez ............... | F16K 99/0001 137/843 |
| 2013/0000759 | A1 * | 1/2013 | Killeen ................... | F04B 49/03 137/565.16 |
| 2014/0356849 | A1 * | 12/2014 | Wikswo ................ | B01L 3/5027 435/1.2 |

\* cited by examiner

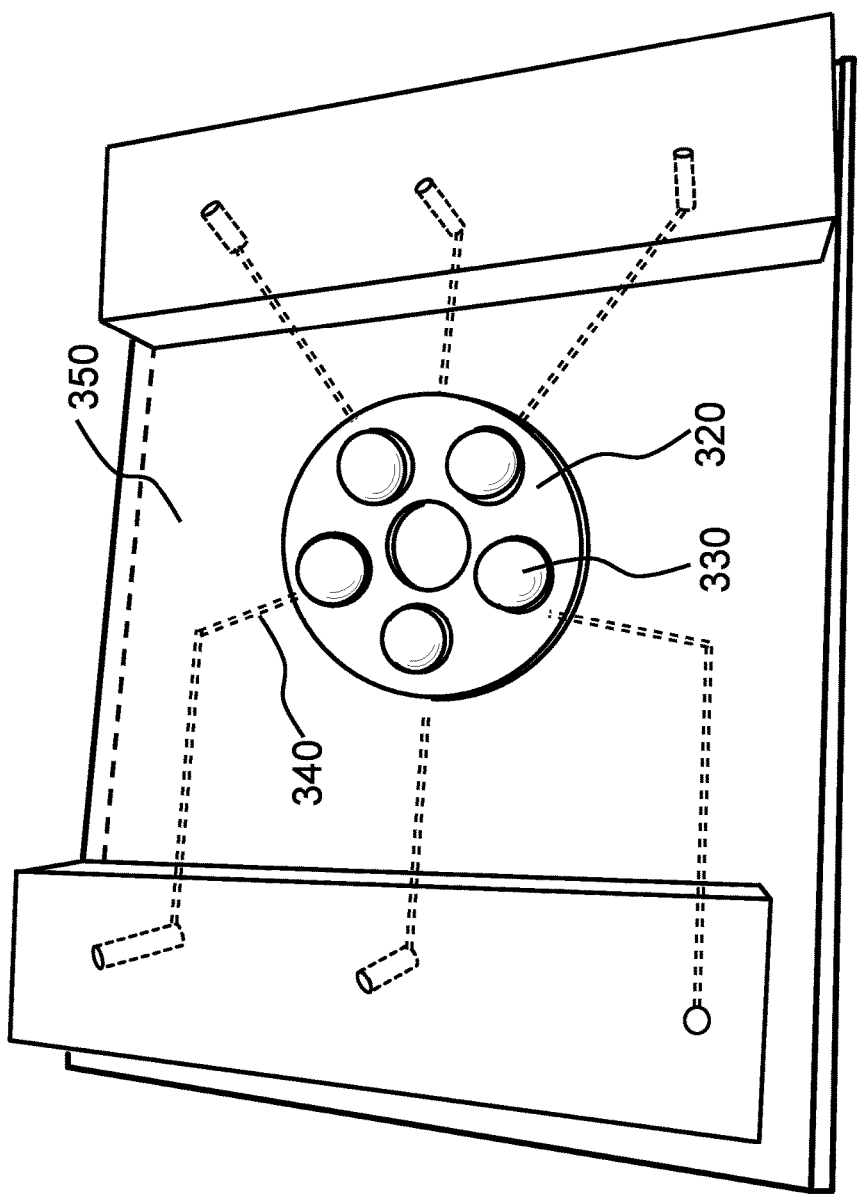

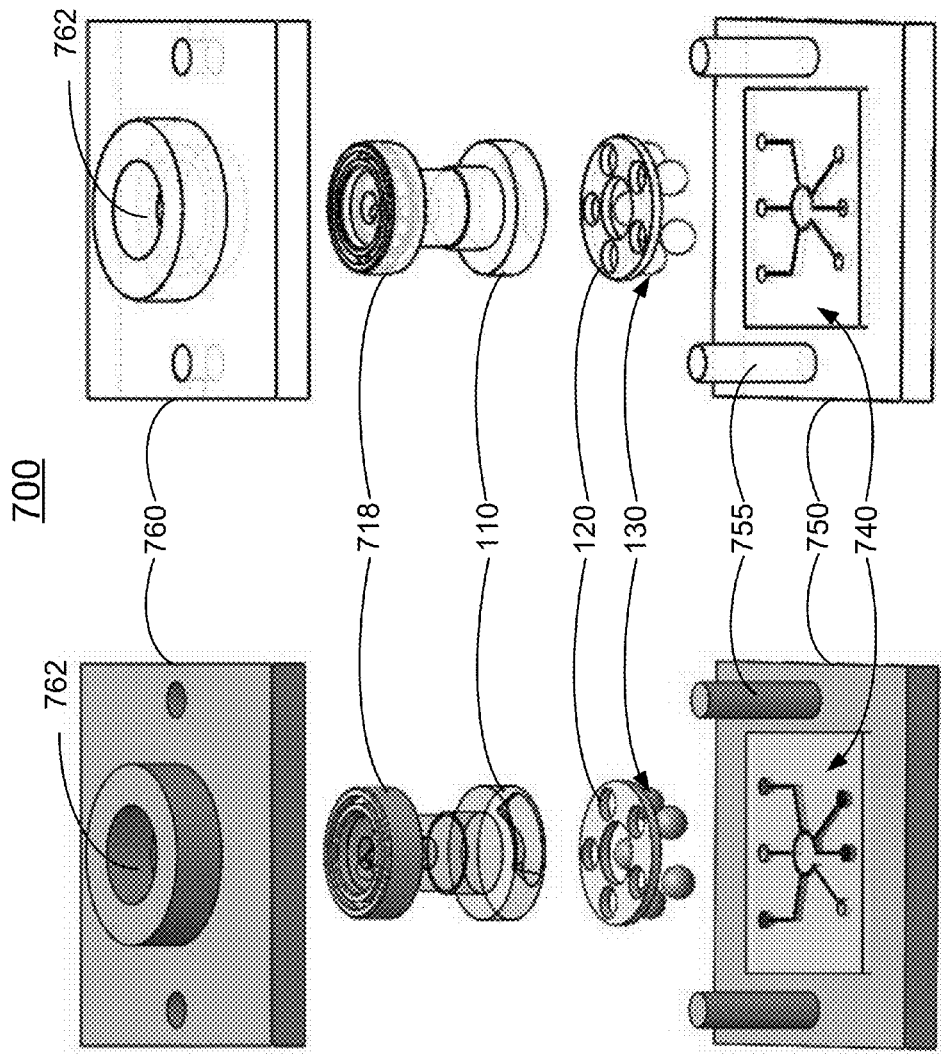

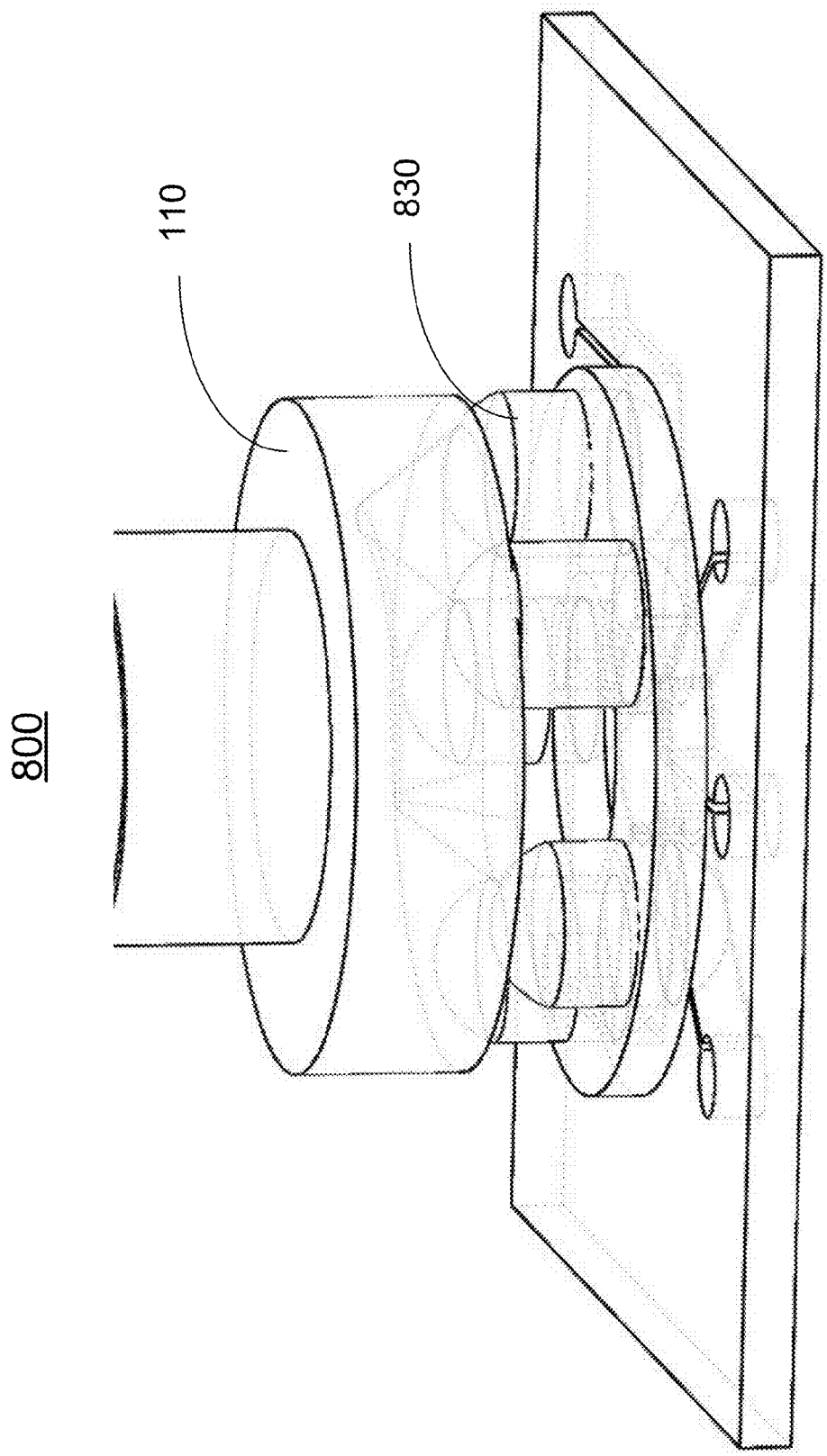

NORMALLY CLOSED MICROVALVE AND APPLICATIONS OF THE SAME

CROSS-REFERENCE TO RELATED PATENT APPLICATIONS

This application claims priority to and the benefit of, pursuant to 35 U.S.C. §119(e), U.S. provisional patent application Ser. No. 61/808,455, filed on Apr. 4, 2013, entitled "IMPROVED RPPM/RPV DESIGNS AND IMPLEMENTATIONS OF SAME", by John P. Wikswo et al., and U.S. provisional patent application Ser. No. 61/822,081, filed on May 10, 2013, entitled "ORGAN ON CHIP INTEGRATION AND APPLICATIONS OF SAME", by John P. Wikswo et al. Each of the above-identified applications is incorporated herein in its entirety by reference.

This application is a continuation-in-part application of PCT application Serial No. PCT/US2013/071026, filed on Nov. 20, 2013, entitled "ORGAN ON CHIP INTEGRATION AND APPLICATIONS OF THE SAME", by Frank E. Block III et al., which itself claims priority to and the benefit of, pursuant to 35 U.S.C. §119(e), U.S. provisional patent application Ser. No. 61/729,149, filed on Nov. 21, 2012, entitled "MICROFLUIDIC FLUID DELIVERY SYSTEMS (VMFDS) AND APPLICATIONS OF SAME", by Frank E. Block III et al., U.S. provisional patent application Ser. No. 61/808,455, filed on Apr. 4, 2013, entitled "IMPROVED RPPM/RPV DESIGNS AND IMPLEMENTATIONS OF SAME", by John P. Wikswo et al., and U.S. provisional patent application Ser. No. 61/822,081, filed on May 10, 2013, entitled "ORGAN ON CHIP INTEGRATION AND APPLICATIONS OF SAME", by John P. Wikswo et al. Each of the above-identified applications is incorporated herein in its entirety by reference.

This application also is a continuation-in-part application of PCT application Serial No. PCT/US2012/068771, filed on Dec. 10, 2012, entitled "INTEGRATED ORGAN-ON-CHIP SYSTEMS AND APPLICATIONS OF THE SAME", by John P. Wikswo et al., which itself claims priority to and the benefit of, pursuant to 35 U.S.C. §119(e), U.S. provisional patent application Ser. No. 61/569,145, filed on Dec. 9, 2011, entitled "PERFUSION CONTROLLER, MICROCLINICAL ANALYZER AND APPLICATIONS OF THE SAME", by John P. Wikswo et al., U.S. provisional patent application Ser. No. 61/697,204, filed on Sep. 5, 2012, entitled "INTELLIGENT CHIP CARRIER AND CHIP CARRIER WITH MICROCHEMICAL ANALYZER AND APPLICATIONS OF THE SAME", by John P. Wikswo et al., and U.S. provisional patent application Ser. No. 61/717,441, filed on Oct. 23, 2012, entitled "INTEGRATED ORGAN MICROFLUIDICS (IOM) CHIP AND APPLICATIONS OF SAME", by John P. Wikswo et al. Each of the above-identified applications is incorporated herein in its entirety by reference.

This application is also a continuation-in-part application of U.S. patent application Ser. No. 13/877,925, filed on Jul. 16, 2013, entitled "PERISTALTIC MICROPUMP AND RELATED SYSTEMS AND METHODS", by Parker A. Gould et al., which is a national phase application under 35 U.S.C. §371 of PCT application Serial No. PCT/US2011/055432, filed on Oct. 7, 2011, entitled "PERISTALTIC MICROPUMP AND RELATED SYSTEMS AND METHODS", by Parker A. Gould et al., which itself claims priority to and the benefit of, pursuant to 35 U.S.C. §119(e), U.S. provisional patent application Ser. No. 61/390,982, filed on Oct. 7, 2010, entitled "PERISTALTIC MICROPUMP AND RELATED SYSTEMS AND METHODS", by Parker A. Gould et al. Each of the above-identified applications is incorporated herein in its entirety by reference.

Some references, which may include patents, patent applications, and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

STATEMENT AS TO RIGHTS UNDER FEDERALLY-SPONSORED RESEARCH

This invention was made with government support under grant numbers NIH 1UH2-TR000491-01, awarded by the National Institutes of Health, DTRA grant HDTRA1-09-1-00-13 and DTRA100271A-5196, awarded by the Defense Threat Reduction Agency, and DARPA contract DARPA-11-73-MPSys-FP-11, awarded by the Defense Advanced Research Projects Agency. The government has certain rights in the invention.

FIELD OF THE INVENTION

The present invention relates generally to valves, and more particularly to a normally closed valve including the selection and delivery of small volumes of fluid and applications of the same.

BACKGROUND OF THE INVENTION

Microfluidics is a rapidly growing field allowing exploratory research in both chemistry and biology. An essential requirement for microfluidic devices is the ability to selectively move a desired fluid from one place to another. To accomplish this, numerous microfluidic pumps and valves have been previously developed. These valves operate on a variety of principles and include pneumatic, thermal, piezoelectric, magnetic, and mechanically actuated valves (Oh et al., A Review of Microvalves, *Journal of Micromechanics & Microengineering*, 16, R13-R39, 2006; Iverson et al., Recent Advances in Microscale Pumping Technologies: A Review and Evaluation, *Microfluidics & Nanofluidics*, 5, 145-174, 2008; Gervais et al., Microfluidic Chips for Point-of-Care Immunodiagnostics, *Advanced Materials*, 23, H151-H176, 2011). The mechanism of action of these valves involves an elastomeric or other interface material between the selected input, unselected inputs, and common output. Existing valves have significant limitations, including switching speed, dead space, undesired fluid mixing, failure, difficulty integrating with microfluidic devices, and cost (Melin et al., Microfluidic Large-Scale Integration, *Annual Review of Biophysics & Biomolecular Structure*, 36, 213-231, 2007).

While previous membrane-compression valves require piezoelectric or electromagnetic actuators, solenoid valves, or pneumatic controllers, this valve design is highly advantageous because it relies on only a rotating drivehead and mechanical support. This drivehead can either be rotated by a simple DC motor, or for manual operation, the DC motor could be replaced with a simple knob or lever. Other manual or motorized rotary compression valves that utilize a screw to clamp a channel closed (e.g., Hulme et al., Incorporation of Prefabricated Screw, Pneumatic, and Solenoid Valves into Microfluidic Devices, *Lab on a Chip*, 9, 79-86, 2009; Weibel et al., Torque-Actuated Valves for Microfluidics, *Analytical Chemistry*, 77, 4726-4733; Markov et al., Tape Underlayment Rotary-Node (TURN) Valves for Simple On-Chip Microfluidic Flow Control, *Biomedical Microdevices*, 12, 135-144, 2010) are not readily capable of switching between multiple inputs and multiple outputs because only one channel is compressed directly at a time.

The classic pneumatically activated microfluidic valve (e.g., Unger et al., Monolithic Microfabricated Valves and Pumps by Multilayer Soft Lithography, *Science*, 288, 113-116, 2000) requires continuous application of pressure to keep the valve closed, and the valve must be connected to a solenoid valve controller. Braille actuators can be used to close an elastomeric membrane valve (e.g., Gu et al., Computerized Microfluidic Cell Culture Using Elastomeric Channels and Braille Displays, *Proceedings of the National Academy of Sciences*, 101, 15861-15866, 2004), but power must be delivered continuously to the Braille actuator to keep the valve closed. PDMS and hybrid PDMS-glass normally closed valves have been created (e.g., Grover et al., Monolithic Membrane Valves and Diaphragm Pumps for Practical Large-Scale Integration into Glass Microfluidic Devices, *Sensors & Actuators B*, 89, 315-323, 2003; Lagally et al., Integrated Portable Genetic Analysis Microsystem for Pathogen/Infectious Disease Detection, *Analytical Chemistry*, 76, 3162-3170, 2004; Schudel et al., Microfluidic Chip for Combinatorial Mixing and Screening of Assays, *Lab on a Chip*, 9, 1676-1680, 2009; Song et al., Computer-Controlled Microcirculatory Support System for Endothelial Cell Culture and Shearing, *Analytical Chemistry*, 77, 3993-3999, 2005; Zhang et al., PMMA/PDMS Valves and Pumps for Disposable Microfluidics, *Lab on a Chip*, 9, 3088-3094, 2009), but as with other pneumatic valves, each valve must be connected to tubing and a solenoid valve, and a source of either pressure or vacuum is required to operate each valve. Whether such membrane valves are either normally open or normally closed, pressure, force, or power must be provided to keep the valve in the opposite state. Furthermore, these pressure-activated diaphragm valves are not readily suited for multi-port, multi-throw interconnection of multiple input and output channels without the use of a large number of coordinated pressure or vacuum controllers.

Therefore, a heretofore unaddressed need exists in the art to address the aforementioned deficiencies and inadequacies.

SUMMARY OF THE INVENTION

In peristaltic pumps and valves disclosed by Parker A. Gould et al. in PCT publication No. WO2012/048261, Wikswo et al. in PCT application Serial No. PCT/US2012/068771, and PCT application Serial No. PCT/US2013/071026, a compression member is moved along a collapsible channel that is a segment of a circle. In the rotary planar peristaltic micropump (RPPM), the collapsible channel is in a planar microfluidic device, such that the rolling of a spherical compression member along a circular path pumps fluid. The rotary planar valve (RPV) is distinguished by the fact that the compression member is moved intermittently to specific locations in the device, rather than continuously as in the RPPM, and that the channels or segments of the RPV channels are perpendicular to the path of the rotating compression members, in contrast to the channels being curved along the path of the rotating compression members in the RPPM. As a result, a compression member can occlude a particular channel by being rotated to a particular angle, thereby serving as a valve. However, this configuration of an RPV is normally open, i.e., fluid is free to flow along any channel not occluded by one of the rotating compression members.

In this invention, the position of the compression members is fixed spatially over the channel to be controlled, and the position of raised or recessed regions in the rotating drivehead determines whether or not a channel is open or closed. This invention also allows a hybrid design, wherein a portion of a channel can be perpendicular to the compression-member path, thereby serving as a valve, and another section of that channel or another channel could be parallel to the path of the compression member, thereby serving as a pump.

In one aspect, the invention relates to a normally closed valve. In one embodiment, the normally closed valve includes a plurality of fluid channels in fluid communication with each other, defined in a flexible base such that when a fluid channel is compressed, a fluid flow through the fluid channel is occluded, otherwise, the fluid flow through the fluid channel is unoccluded. In one embodiment, the flexible base is formed of an elastic material. In one embodiment, the elastic material includes polydimethylsiloxane (PDMS).

Further, the normally closed valve includes an actuator comprising a cage defining a plurality of spaced-apart openings, and a plurality of pop-up members, each pop-up member retained in a respective opening of the cage and being vertically movable therein. The actuator is placed on the flexible base to constrain each pop-up member in a position immediately above a respective fluid channel, such that when a pop-up member is pressed into the flexible base, a fluid channel that is immediately beneath the pop-up member is compressed, otherwise, the fluid channel is uncompressed.

In one embodiment, each of the plurality of pop-up members comprises a ball.

In one embodiment, each of the plurality of pop-up members comprises a cylinder whose end portions have convex curved surfaces, such that as assembled, one end portion is proximal to a respective fluid channel and the other end portion is engaged with the drivehead. The end portions are shaped like a ball, spheroid, a segment of a sphere, or other smoothly convex curved onjects to prevent damage to the flexible base.

In another embodiment, each of the plurality of pop-up members comprises a head portion, a body extending from the head portion, and a rolling member attached to the body, such that as assembled, the head portion is proximal to a respective fluid channel and the rolling member is rotatably engaged with the drivehead. Each of the plurality of pop-up members may further comprise an alignment mechanism for maintaining alignment of the roller member.

In one embodiment, the rolling member comprises a ball, roller, or a wheel. In one embodiment, the body comprises a spring or Belleville washer.

In one embodiment, each of the plurality of pop-up members is coated with a wear-resistant or lubricating film.

In addition, the normally closed valve also includes a drivehead having a surface and at least one recess formed on the surface. The drivehead is rotatably engaged with the actuator such that each pop-up member is pressed into the flexible base normally, and as the drivehead rotates, any selected pop-up member is unpressed when the at least one recess arrives and pressed as the at least one recess departs, thereby selectively unoccluding or occluding a fluid flow through a desired fluid channel.

In one embodiment, the at least one recess comprises at least one teardrop-shaped groove located along single or multiple concentric rings surrounding a rotational axis of the drivehead. The at least one teardrop-shaped groove may have sloped sidewalls with fixed or variable taper-rates such that when the drivehead rotates at predetermined rotation angles, the at least one teardrop-shaped groove is positioned over a pop-up member so as to partially unocclude or completely unocclude its underlying channel, and at other rotation angles, the at least one teardrop-shaped groove is displaced from the pop-up member so as to completely occlude its underlying channel.

In one embodiment, the drivehead is driven by a motor.

In one embodiment, the drivehead has a first cylindrical portion on which the recess is formed, and a second cylindrical portion extending coaxially from the first cylindrical portion, wherein the first cylindrical portion has a diameter that is greater than that of the second cylindrical portion, and wherein the second cylindrical portion is engaged with the motor.

In one embodiment, the normally closed valve further includes a bearing rotatably attached onto the second cylindrical portion of the drivehead; and a tension holding plate having an opening formed to accommodate the bearing, adjustably mounted to alignment pins for transferring tensioning pressure via the bearing to the fluidic channels thereunder, wherein the alignment pins are vertically positioned in relation to the flexible base such that each pop-up member of the actuator is aligned with the respective fluid channel thereunder and the drivehead is rotatably engaged with the actuator.

Additionally, the normally closed valve also includes at least one offset fluid channel in fluid communication with the plurality of fluid channels, formed in the flexible base and offsetting the plurality of pop-up members of the actuator.

In another aspect, the invention relates to a normally closed valve. In one embodiment, the normally closed valve includes a plurality of fluid channels in fluid communication with each other, defined in a flexible base formed of an elastic material such that when a fluid channel is compressed, a fluid flow through the fluid channel is occluded, otherwise, the fluid flow through the fluid channel is unoccluded; and means for selectively compressing or uncompressing a desired fluid channel.

In one embodiment, the selectively compressing or uncompressing means comprises a drivehead having a surface and at least one recess formed on the surface.

In one embodiment, the selectively compressing or uncompressing means further comprises an actuator comprising a plurality of resilient structures, placed on the flexible base to position each resilient structure immediately above a respective fluid channel, such that when a resilient structure is pressed into the flexible base, a fluid channel that is immediately beneath the pop-up member is compressed, otherwise, the fluid channel is uncompressed; wherein the drivehead is rotatably engaged with the actuator such that each resilient structure is pressed into the flexible base normally, and as the drivehead rotates, any selected resilient structure is unpressed when the at least one recess arrives and pressed as the at least one recess departs, thereby selectively unoccluding or occluding a fluid flow through a desired fluid channel. In one embodiment, each resilient structure comprises a cantilever radially extending from a central portion of the actuator, and a rolling member attached to the cantilever, wherein the cantilever has a head portion adapted to press or unpress the flexible base, and the rolling member is rotatably engaged with the drivehead. In one embodiment, each resilient structure is formed of an elastic material that is the same as or a different material from that of the flexible base.

In another embodiment, the selectively compressing or uncompressing means further comprises an actuator comprising a cage defining a plurality of spaced-apart openings, and a plurality of pop-up members, each pop-up member retained in a respective opening of the cage and being vertically movable therein, wherein the actuator is placed on the flexible base to constrain each pop-up member in a position immediately above a respective fluid channel, such that when a pop-up member is pressed into the flexible base, a fluid channel that is immediately beneath the pop-up member is compressed, otherwise, the fluid channel is uncompressed, wherein the drivehead is rotatably engaged with the actuator such that each pop-up member is pressed into the flexible base normally, and as the drivehead rotates, any selected pop-up member is unpressed when the at least one recess arrives and pressed as the at least one recess departs, thereby selectively unoccluding or occluding a fluid flow through a desired fluid channel.

In one embodiment, each of the plurality of pop-up members is coated with a wear-resistant or lubricating film.

In one embodiment, each of the plurality of pop-up members comprises a ball.

In another embodiment, each of the plurality of pop-up members comprises a head portion, a body extending from the head portion, and a rolling member attached to the body, such that as assembled, the head portion is proximal to a respective fluid channel and the rolling member is rotatably engaged with the drivehead. In one embodiment, each of the plurality of pop-up members further comprises an alignment mechanism for maintaining alignment of the roller member.

In one embodiment, the rolling member comprises a ball, roller, or a wheel.

In one embodiment, the body comprises a spring or Belleville washer.

In one embodiment, the at least one recess comprises at least one teardrop-shaped groove located along single or multiple concentric rings surrounding a rotational axis of the drivehead, wherein the at least one teardrop-shaped groove has sloped sidewalls with fixed or variable taper-rates.

In one embodiment, the rolling members are actuated by at least one circular concentric variable-depth groove or, alternatively, a variable-depth ridge attached to the drivehead in such a manner as to provide varying degrees of actuation of the pop-up members as a function of the rotation angle of the drivehead.

In one embodiment, the rolling members are actuated by at least one circular concentric variable-depth groove or, alternatively, a variable-depth ridge attached to the drivehead in such a manner as to provide varying degrees of actuation of the pop-up members as a function of the rotation angle of the drivehead. In this embodiment, the number and positioning of the variable height or depth regions of the concentric grooves or concentric ridges can be arranged in such a way that when the drivehead is rotated to certain specific rotational angles, some combination of the multiple fluidic channels can be fully occluded, partially occluded, or fully un-occluded.

In one embodiment, the drivehead is driven by a motor.

In one embodiment, the drivehead has a first cylindrical portion on which the recess is formed, and a second cylindrical portion extending coaxially from the first cylindrical portion, wherein the first cylindrical portion has a diameter that is greater than that of the second cylindrical portion, and wherein the second cylindrical portion is engaged with the motor.

In one embodiment, the normally closed valve further includes a bearing rotatably attached onto the second cylindrical portion of the drivehead; and a tension holding plate having an opening formed to accommodate the bearing, adjustably mounted to alignment pins for transferring tensioning pressure via the bearing to the fluidic channels thereunder, wherein the alignment pins are vertically positioned in relation to the flexible base such that each pop-up member of the actuator is aligned with the respective fluid channel thereunder and the drivehead is rotatably engaged with the actuator.

In one embodiment, multiple pop-up members are arranged in such a manner that a series of three or more adjacent pop-up members are spaced so that their sequential compression and decompression in a serial manner serve as a peristaltic pump moving fluid in a direction determined by the direction of rotation of the drivehead.

In an extension of this concept, in another embodiment, the fluid being pumped by the sequential pop-up members is controlled by other pop-up members that serve as normally closed valves.

In another embodiment utilizing the combined pumping/valve functions of multiple pop-up members, the pumping section can force fluid into a chamber with a distensible elastomeric membrane such that the fluid is pressurized at the end of the pumping cycle. As the drivehead rotates further, the release of another pop-up member that serves as a normally closed valve can release this pressurized fluid into another channel.

In addition, the normally closed valve may also have at least one offset fluid channel in fluid communication with the plurality of fluid channels, formed in the flexible base and offsetting the selectively compressing or uncompressing means.

In yet another aspect, the invention relates to a system comprising one or more normally closed valves disclosed above.

In a further aspect, the invention relates to a method for selectively occluding or unoccluding a fluid flow through a desired fluid channel. In one embodiment, the method includes providing a plurality of fluid channels in fluid communication with each other, wherein the plurality of fluid channels is defined in a flexible base and configured such that when a fluid channel is compressed, a fluid flow through the fluid channel is occluded, otherwise, the fluid flow through the fluid channel is unoccluded; and selectively compressing or uncompressing the desired fluid channel.

In one embodiment, the step of selectively compressing or uncompressing the desired fluid channel is performed with an actuator driven by a drivehead having a surface and at least one recess formed on the surface.

In one embodiment, the actuator comprises a plurality of resilient structures, placed on the flexible base to position each resilient structure immediately above a respective fluid channel, such that when a resilient structure is pressed into the flexible base, a fluid channel that is immediately beneath the pop-up member is compressed, otherwise, the fluid channel is uncompressed, and wherein the drivehead is rotatably engaged with the actuator such that each resilient structure is pressed into the flexible base normally, and as the drivehead rotates, any selected resilient structure is unpressed when the at least one recess arrives and pressed as the at least one recess departs, thereby selectively unoccluding or occluding a fluid flow through the desired fluid channel.

In another embodiment, the actuator comprises a cage defining a plurality of spaced-apart openings, and a plurality of pop-up members, each pop-up member retained in a respective opening of the cage and being vertically movable therein, wherein the actuator is placed on the flexible base to constrain each pop-up member in a position immediately above a respective fluid channel, such that when a pop-up member is pressed into the flexible base, a fluid channel that is immediately beneath the pop-up member is compressed, otherwise, the fluid channel is uncompressed, wherein the drivehead is rotatably engaged with the actuator such that each pop-up member is pressed into the flexible base normally, and as the drivehead rotates, any selected pop-up member is unpressed when the at least one recess arrives and pressed as the at least one recess departs, thereby selectively unoccluding or occluding a fluid flow through the desired fluid channel.

In another embodiment, the actuator comprises a cage defining a plurality of spaced-apart openings, and a plurality of pop-up members, each pop-up member retained in a respective opening of the cage and being vertically movable therein, wherein the actuator is placed on the flexible base to constrain each pop-up member in a position immediately above a respective fluid channel, such that when a pop-up member is pressed to a variable extent into the flexible base, a fluid channel that is immediately beneath the pop-up member is fully or partially occluded, otherwise, when the pop-up member is not being pressed by the variable-depth concentrically located features built into the drivehead the fluid channel is uncompressed. The drivehead concentrically located variable-depth features rotatably engaged with each actuator can be arranged such that each individual pop-up member is pressed into the flexible base, to a greater or lesser degree depending on the exact rotational position of the drivehead, and as the drivehead rotates, any selected pop-up member can be unpressed, fully pressed, or partially pressed, resulting respectively in the individual channel being unoccluded, fully occluded, or partially occluded.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIG. 3A shows a flexible base having fluid channels and an actuator utilized in a normally closed valve according to one embodiment of the invention.

FIGS. 7A-7D show schematically a normally closed valve according to one embodiment of the invention.

FIGS. 8A and 8B show schematically a normally closed valve with actuator pins according to one embodiment of the invention.

DETAILED DESCRIPTION OF THE INVENTION

Figure 1A:
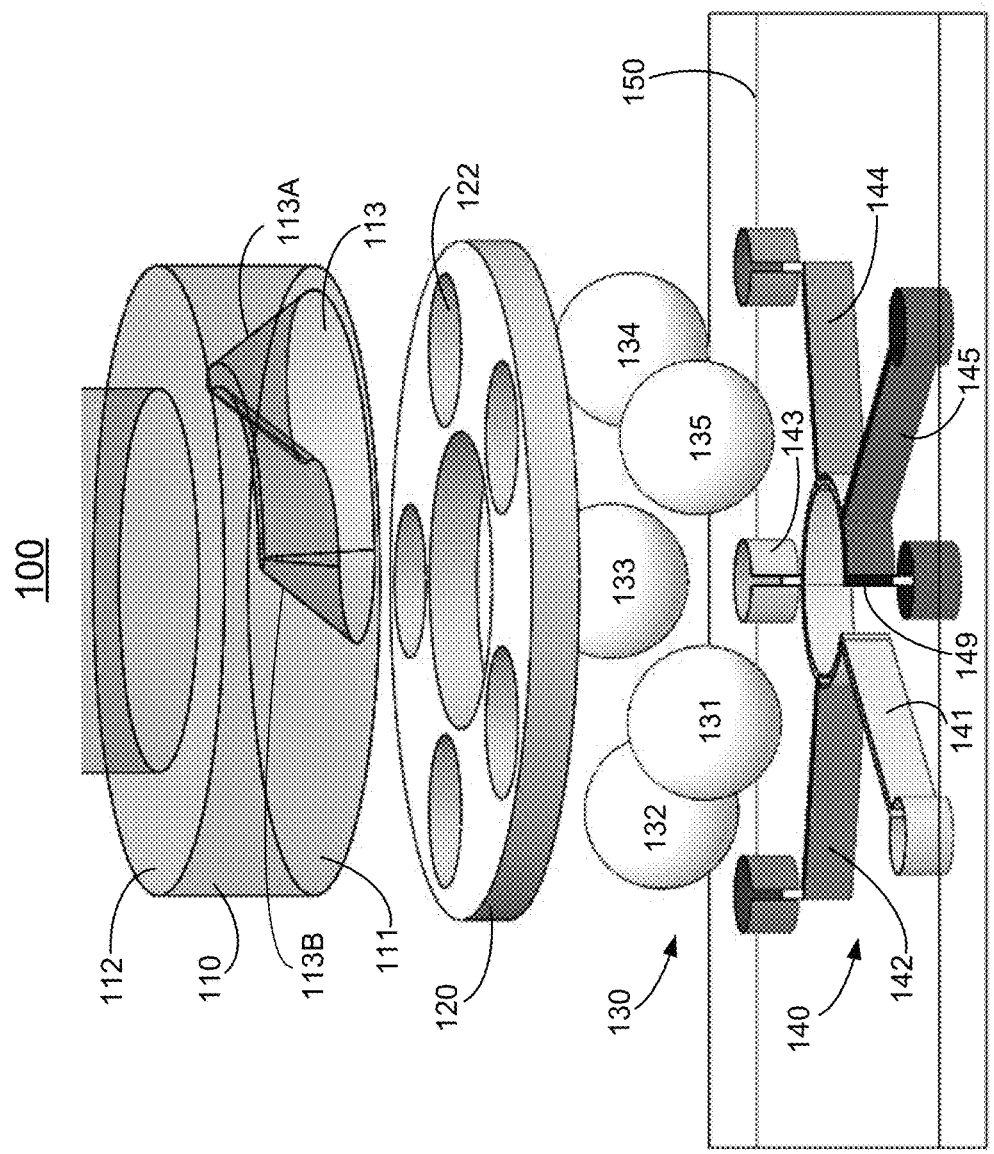
FIGS. 1A and 1B show schematically a normally closed valve according to one embodiment of the invention.

The present invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present invention.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on "upper" sides of the other elements. The exemplary term "lower" can, therefore, encompass both an orientation of "lower" and "upper", depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about", "substantially" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

As used herein, the terms, "fluidic path" and "fluidic channel" are exchangeable, and refer to a passage, a conduit, a groove, a furrow, or the like that allow a fluid flow through it.

The description is now made as to the embodiments of the present invention in conjunction with the accompanying drawings. In accordance with the purposes of this invention, as embodied and broadly described herein, this invention relates to a normally closed valve and applications of the same.

The normally closed valve according to the invention is improvements over a Rotary Planar Valve (RPV) disclosed by Parker A. Gould et al. in PCT publication No. WO2012/048261, Wikswo et al. in PCT application Serial No. PCT/US2012/068771, and PCT application Serial No. PCT/US2013/071026, where all of the fluid channels are open to fluid flow during transition from one position to another. However, in the normally closed valve of this invention, all of the fluid channels are closed during changing from one valve position to another, except for the channel located beneath the teardrop; i.e., the improvement to the RPV is that all channels in the valve are now normally closed, and only a single channel is actuated as desired. More important, this valve design can maintain its normally closed state or a selected open state with no delivery of external force, pressure, or power. This type of low dead volume valve is suitable for use in many of the modules and systems, such as the Perfusion Controller, MicroClinical Analyzer, and Microformulator, disclosed by Wikswo et al. in PCT application Serial No. PCT/US2012/068771, and PCT application Serial No. PCT/US2013/071026.

In one aspect of the invention, the normally closed valve includes a plurality of fluid channels defined in a flexible base formed of an elastic material such that when a fluid channel is compressed, a fluid flow through the fluid channel is occluded, otherwise, the fluid flow through the fluid channel is unoccluded; and means for selectively compressing or uncompressing a desired fluid channel. The means includes a drivehead and an actuator as discussed below.

In certain embodiments, the normally closed valve operates under the principle that ball bearings are compressing a flexible base polymer with an embedded fluid channel or tube in such a way as to occlude fluid flow. These ball bearings are retained in a cage to prevent rotational or horizontal movement. The balls are free to move in the vertical direction but are constrained to their intended position immediately above the associated channel A compression drivehead is located above the ball bearings. A recess or teardrop-shaped groove is formed in the drivehead such that a ball located beneath the groove rises into the groove because of the restoring force of the elastomeric material, thus opening the channel. As the drivehead rotates, any selected ball will experience decompression (be unpressed) when the groove arrives and compression (be pressed) as the groove departs, such that the drivehead rotates smoothly.

An alternative embodiment of the normally closed valve includes an arrangement of gate valves around a common output port in which each gate valve is in the normally closed (compressed) state. An actuator above the valve moves in such a way that the compression force is no longer applied to the gate valve, allowing the gate to rise and fluid to flow freely. In one embodiment, each valve is operated by its own actuator.

In some embodiments, a first, second, or more fluids are in communication with an outlet such that a selected, and only a selected, input flows freely to the output.

Figure 10:
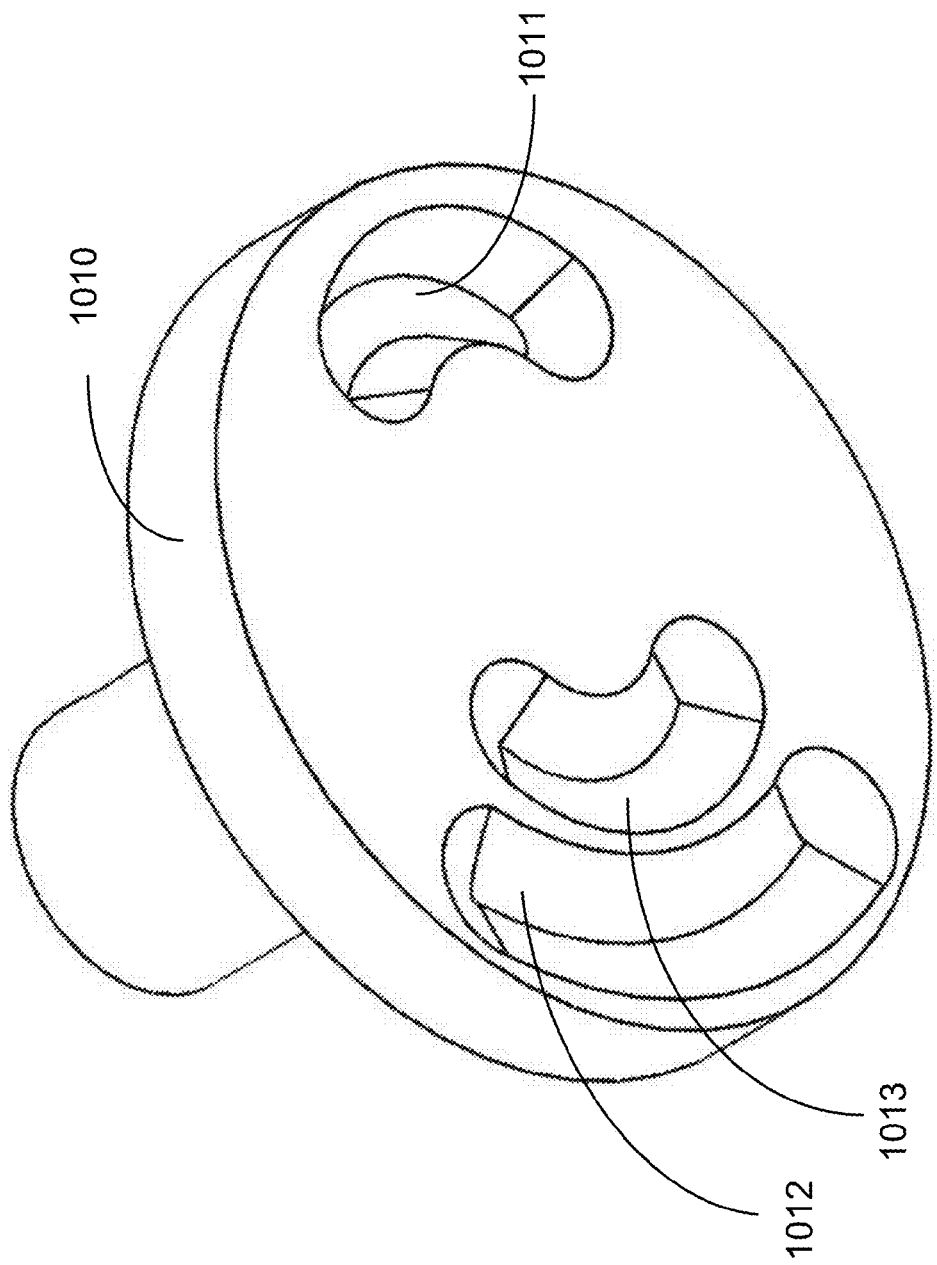
FIG. 10 shows schematically a drivehead utilized in a valve or pump according to one embodiment of the invention.

According to the invention, variations of the normally closed rotary fluidic valve include, but are not limited to:
1) Normally closed valve assemblies that use structures permanently embedded in the PDMS (or other elastic polymer) to substitute for the individual precisely located ball bearing structures used in our original proof of concept design. These structures "pop up" into the recess built into the rotary compression drivehead in order to open the channel normally compressed under the structure. These pop-up structures can be fabricated into the elastic polymer at the same time as the channels are molded, thus simplifying the design and assembly of the device. A fixed alignment ring is attached to the base membrane to automatically align the actuators above the channels.
2) Normally closed valve assemblies that use molded polymer structures as the pop-up features. The polymer used could be of the same type as the elastic polymer used to mold the fluidic channels or of a different type.
3) Normally closed valve assemblies that incorporate a plurality of pop-up teardrop style recesses in the rotating compression head, thus enabling more complex switch designs, including multi-pole, multi-position designs. The multiple teardrop style recesses can be located along single or multiple concentric rings surrounding the drive structure, as shown in FIG. 10.
4) Dual tapered teardrop design recesses that allow the drive shaft to move either clockwise or counter-clockwise.
5) Variable taper-rate teardrop designs that allow partial closure of underlying channels. At some shaft rotation angles the valve could be totally closed, and at other rotation angles the selected channel could be partially open or completely open. This feature allows for continuous-value, analog control of channel resistance.
6) Normally closed valve assemblies in which the pop-up structure has been coated with a wear-resistant or lubricating film.
7) Normally closed valve where the actuator comprises rollers or other mechanical means to prevent wear on the compression drivehead.
8) Normally closed valve where the actuators have integrated springs or Belleville washers to absorb shock while opening or closing the actuator and to provide a controlled compressive force when operating in the closed position.
9) Normally closed valve assemblies in which the pop-up members are actuated by at least one circular concentric variable-depth groove or, alternatively, a variable-depth ridge attached to the drivehead in such a manner as to provide varying degrees of actuation of the pop-up members as a function of the rotation angle of the drivehead, as shown in FIG. 10. The number and positioning of the variable height or depth regions of the concentric grooves or concentric ridges can be arranged in such a way that when the drivehead is rotated to certain specific rotational angles, some combination of the multiple fluidic channels can be fully occluded, partially occluded, or fully un-occluded.

10) Multiple pop-up members arranged in such a manner that a series of three or more adjacent pop-up members are spaced so that their sequential compression and decompression in a serial manner serve as a peristaltic pump moving fluid in a direction determined by the direction of rotation of the drivehead.

11) Utilizing the combined pumping/valve functions of multiple pop-up members where the pumping section can force fluid into a chamber with a distensible elastomeric membrane such that the fluid is pressurized at the end of the pumping cycle. As the drivehead rotates further, the release of another pop-up member that serves as a normally closed valve can release this pressurized fluid into another channel.

These and other aspects of the present invention are further described in the following section. Without intending to limit the scope of the invention, further exemplary implementations of the same according to the embodiments of the present invention are given below.

Figure 1B:
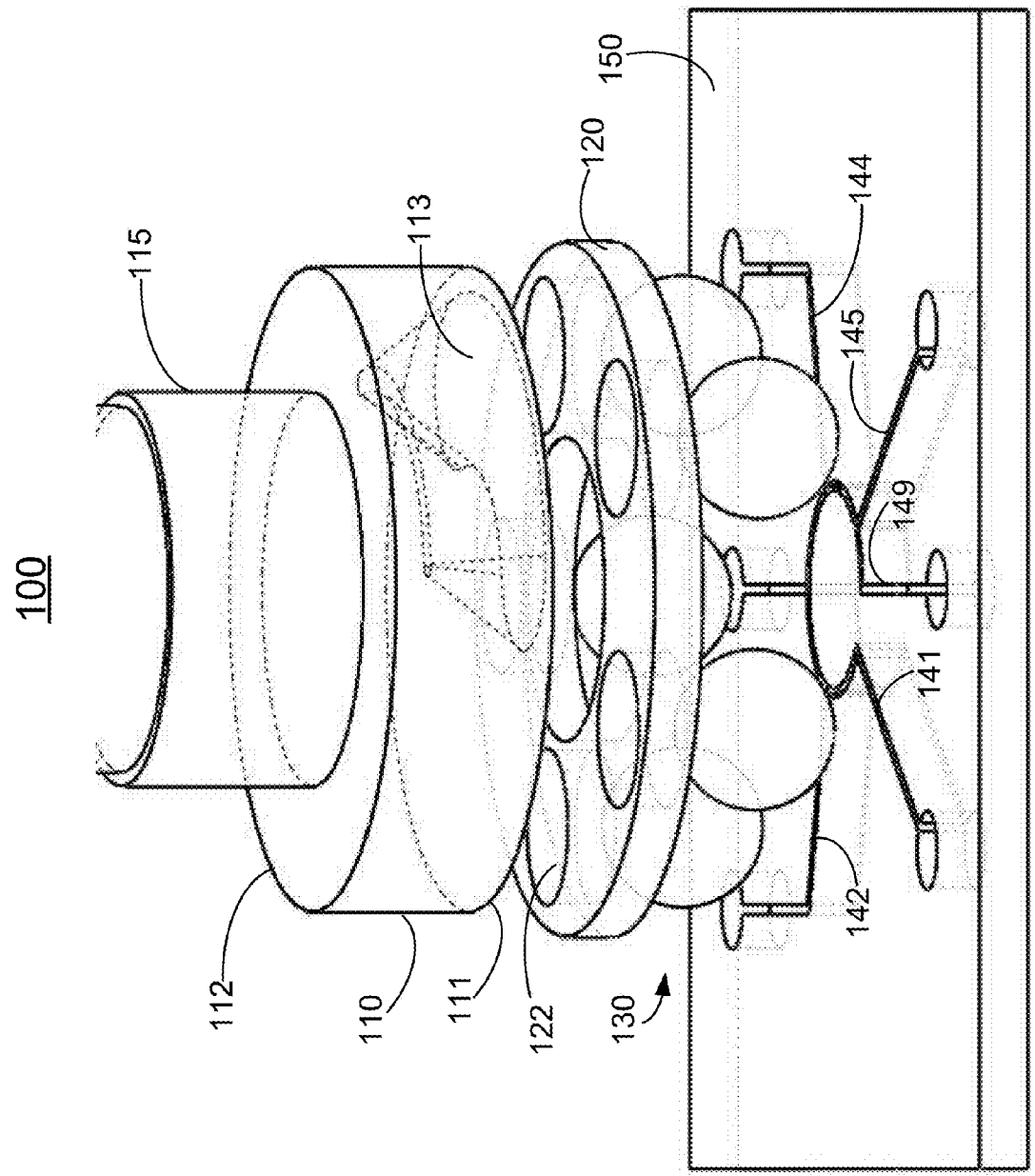
Figure 1C:
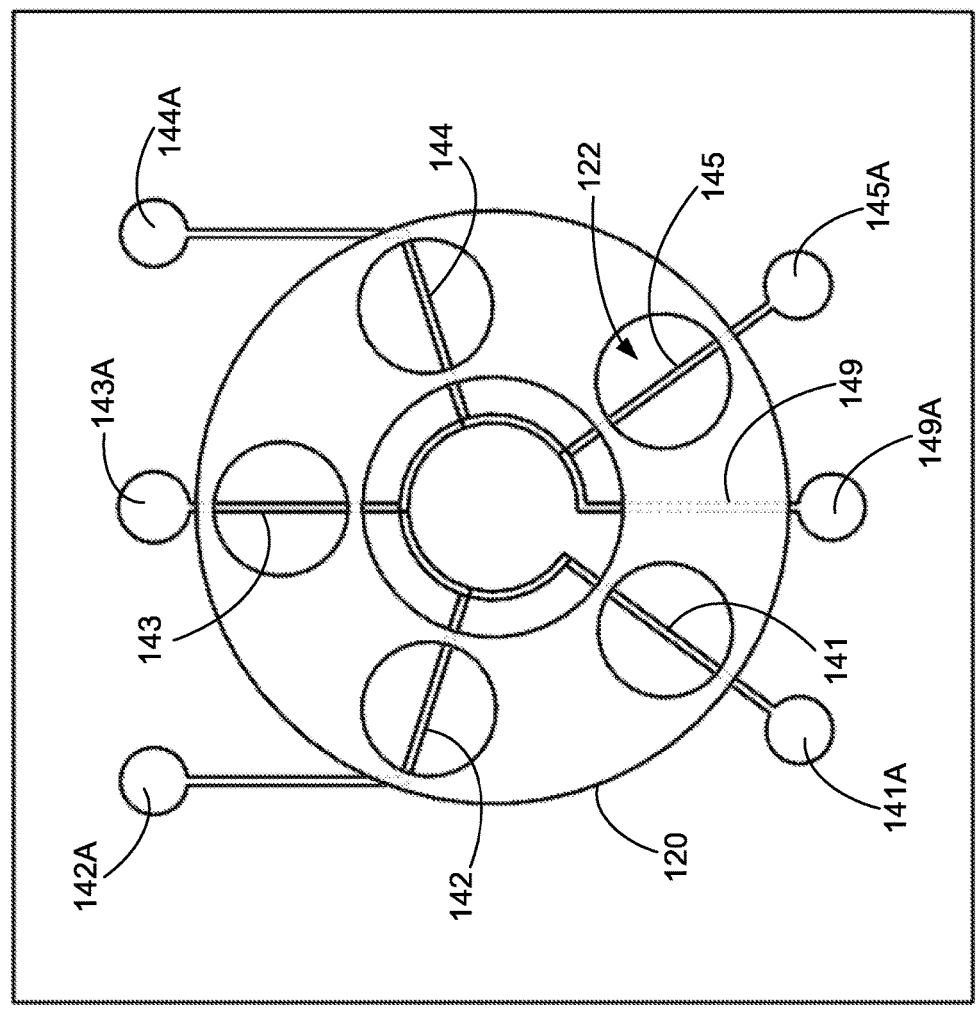
FIG. 1C shows schematically a layout of fluid channels utilized in the normally closed valve shown in FIGS. 1A and 1B.

Referring to FIG. 1, a normally closed valve 100 is shown according to one embodiment of the invention. The normally closed valve 100 includes a plurality of fluid channels 140, an actuator and a drivehead 110. The plurality of fluid channels 140 is defined in a flexible base 150 and is in fluid communication with each other through a central output channel 149. The flexible base 150 is formed of an elastic material, for example an elastic polymer, such as PDMS, or other elastic materials. As such, when a fluid channel is compressed or pressed, a fluid flow through the fluid channel can be partially or completely occluded, depending upon the amount of the compression exerted on the channel. If the fluid channel is sufficiently compressed or pressed so that the fluid channel is completely closed, no fluid flow through the fluid channel would be allowed, i.e., the fluid channel is in a completely closed state. If the fluid channel is compressed or pressed, but not sufficiently compressed or pressed so that the fluid channel is partially closed and partially opened, a fluid can flow through the partially opened fluid channel, i.e., the fluid channel is in a partially closed state or a partially opened state. When the fluid channel is uncompressed or unpressed, a fluid can freely flow through the fluid channel, i.e., the fluid channel is in a completely opened state. In this exemplary embodiment, the plurality of fluid channels 140 includes five fluid channels 141-145. It should be noted that other numbers of the fluid channels can also be utilized to practice the invention.

Additionally, the normally closed valve 100 also includes at least one offset fluid channel 149 in fluid communication with the fluid channels 141-145, formed in the flexible base 150 and offsetting the pop-up members 130 of the actuator.

As shown in FIG. 1, the actuator includes a cage 120 defining a plurality of spaced-apart openings 122, and a plurality of pop-up members such as ball bearings 130. Each ball bearing 131-135 is retained in a respective opening 122 of the cage 120 and is vertically movable therein. For the purpose of illustration, five openings and five ball bearings 131-135 are selected. Again, other numbers of the openings and ball bearings can also be utilized to practice the invention.

The actuator is placed on the flexible base 150 to constrain each ball bearing in a position immediately above a respective fluid channel. For example, the ball bearings 131-135 are positioned immediately over the channels 141-145, respectively. As such, when a ball is pressed into the flexible base 150, the corresponding fluid channel is compressed. Otherwise, the fluid channel is uncompressed.

The drivehead 110 has a first surface 111, an opposite, second surface 112, and at least one recess formed on the first surface 111. The at least one recess comprises at least one teardrop-shaped groove located along single or multiple concentric rings surrounding a rotational axis of the drivehead 110. In this exemplary embodiment, the at least one teardrop-shaped groove includes one teardrop-shaped groove 113. The teardrop-shaped groove 113 has sloped sidewalls 113A with fixed or variable taper-rates. When the drivehead 110 rotates at predetermined rotation angles, the teardrop-shaped groove 113 positions over a ball bearing so as to partially unocclude or completely unocclude its underlying channel. This feature allows for continuous-value, analog control of channel resistance. When the drivehead 110 rotates at the other rotation angles, the teardrop-shaped groove 113 displaces from the ball bearing which completely occludes its underlying channel.

The drivehead is rotatably and operably engaged with the actuator such that each ball bearing is pressed into the flexible base 150 normally, i.e., maintaining the channel in a normally closed state. As the drivehead 110 rotates, any selected ball bearing experiences uncompression (is unpressed) when the groove 113 arrives and compression (is pressed) as the groove departs, thereby selectively unoccluding or occluding a fluid flow through a desired fluid channel.

The drivehead 110 can be driven by a motor or manually.

Figure 2A:
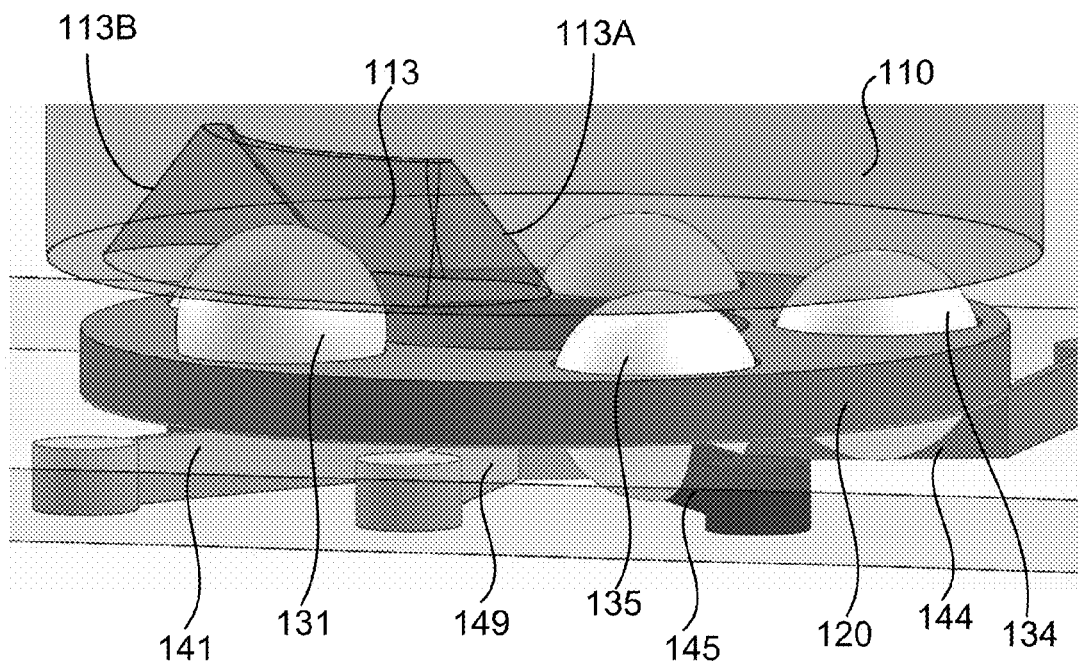
FIGS. 2A-2D show operably the opening and closing of a fluidic channel in the normally closed valve shown in FIGS. 1A and 1B.

The operations of the normally closed valve 100 are illustrated in FIGS. 2A-2D, showing a series of the opening and closing of a fluidic channel. As shown in FIG. 2A, when the drivehead 110 rotates such that the groove is located over the ball 131, the ball 131 is popped up due to the restoring force of the elastomeric base 150 and the channel 141 beneath the ball 131 is uncompressed, while the other balls 132-135 are pressed into the flexible base 150 and the other channels 142-145 are compressed. Accordingly, the channel 141 is in the opened state, while the other channels are in the closed state.

Figure 2B:
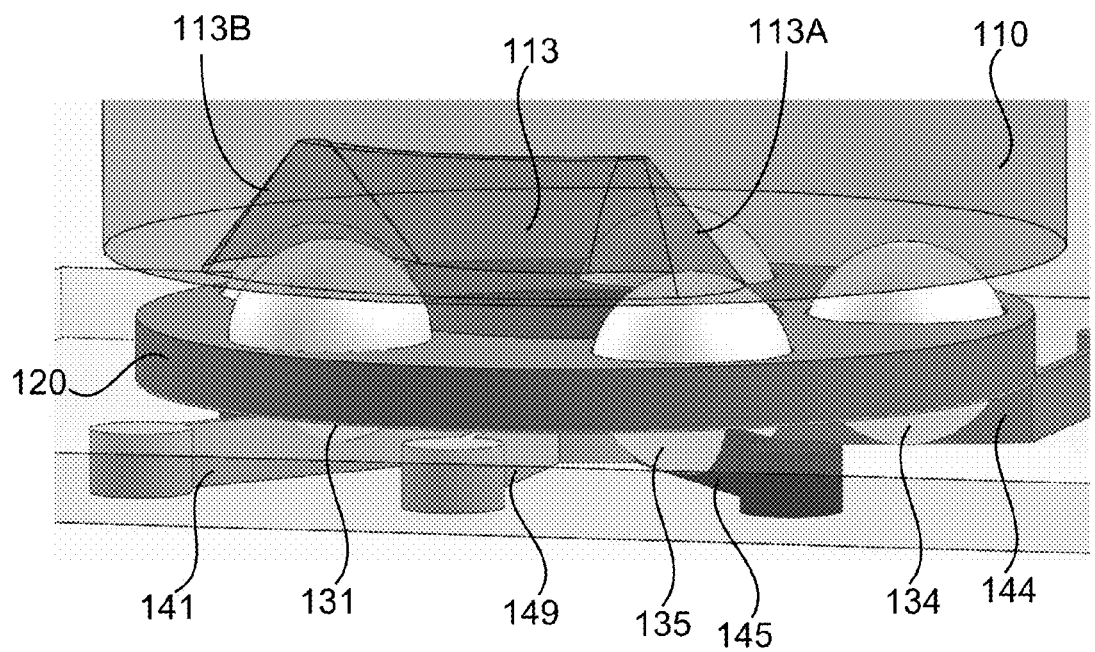
Figure 2C:
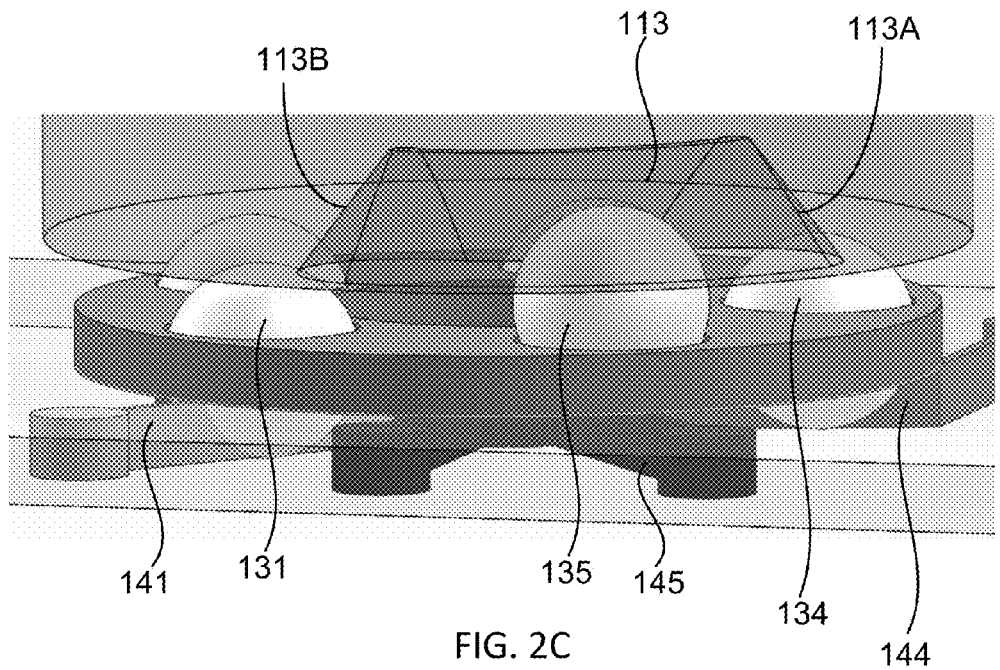
Figure 2D:
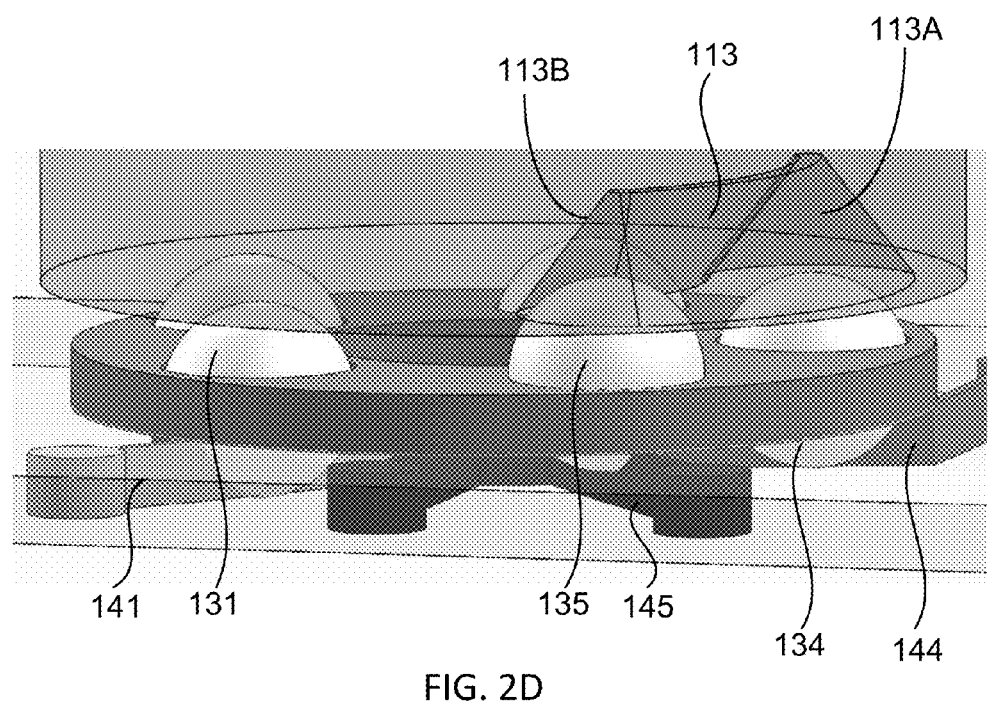

As the drivehead 110 further rotates, as shown in FIG. 2B, the groove 113 moves towards the ball 135, the tapered walls at the rear end of the groove 113 are recompressing the ball 131 while the tapered walls at the front end are uncompressing the ball 135. In this position, both the channels 141 and 145 may be partially compressed and thus in the partially closed state. When the drivehead 110 rotates to a position as shown in FIG. 2C, the ball 135 is popped up into the groove 113 and thus the channel 145 is in the completely opened state. The other channels 141-144 are in the completely closed state. FIG. 2D shows the recompressing of the ball 135 above the channel 145, and the uncompressing of the ball 134 above the channel 144. The channels 145 and 144 may be in a partially opened or closed state. Similarly, by rotating the drivehead at a predetermined rotation angle, a channel can be selectively in the completely opened state, the completely closed state, or the partially opened or closed state.

Figure 3B:
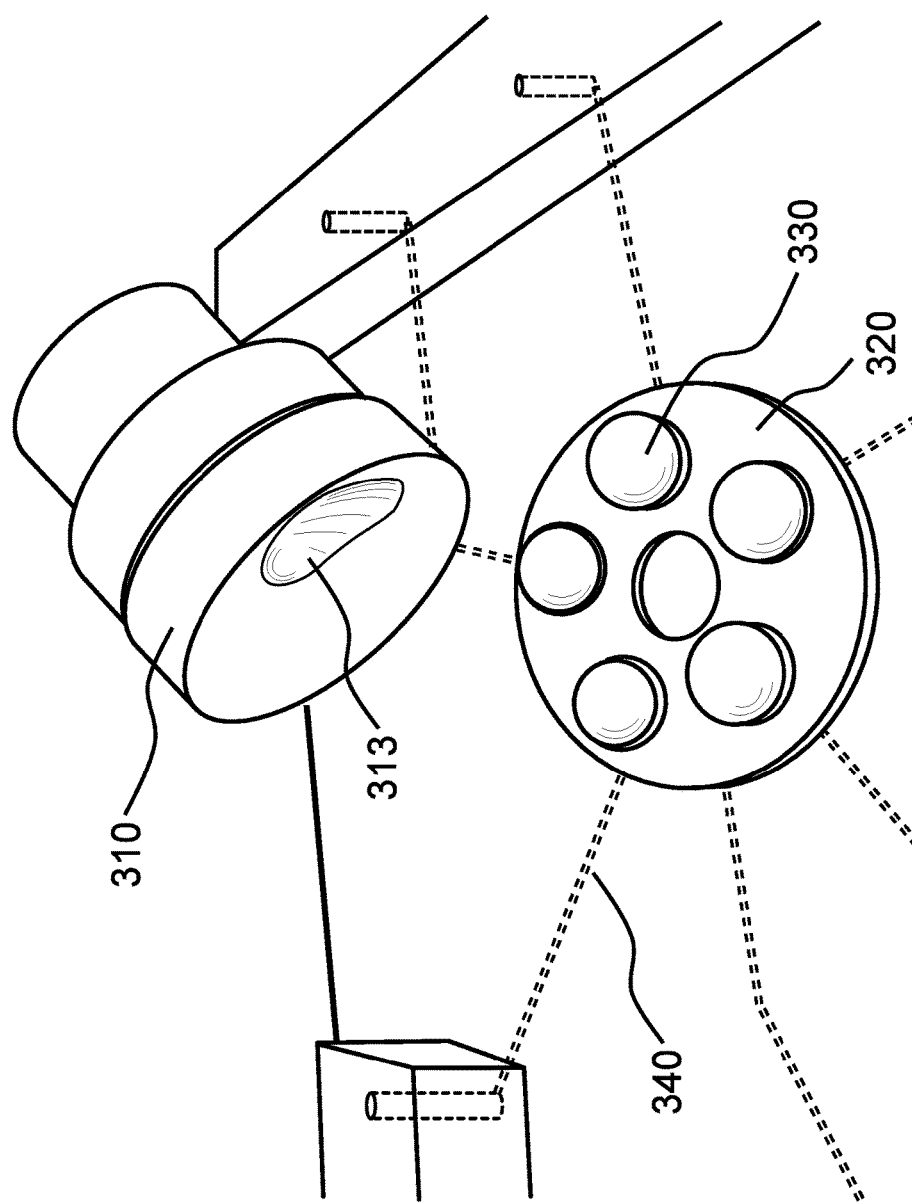
FIG. 3B shows a flexible base having fluid channels, an actuator and a drivehead utilized in a normally closed valve according to one embodiment of the invention.
Figure 3C:
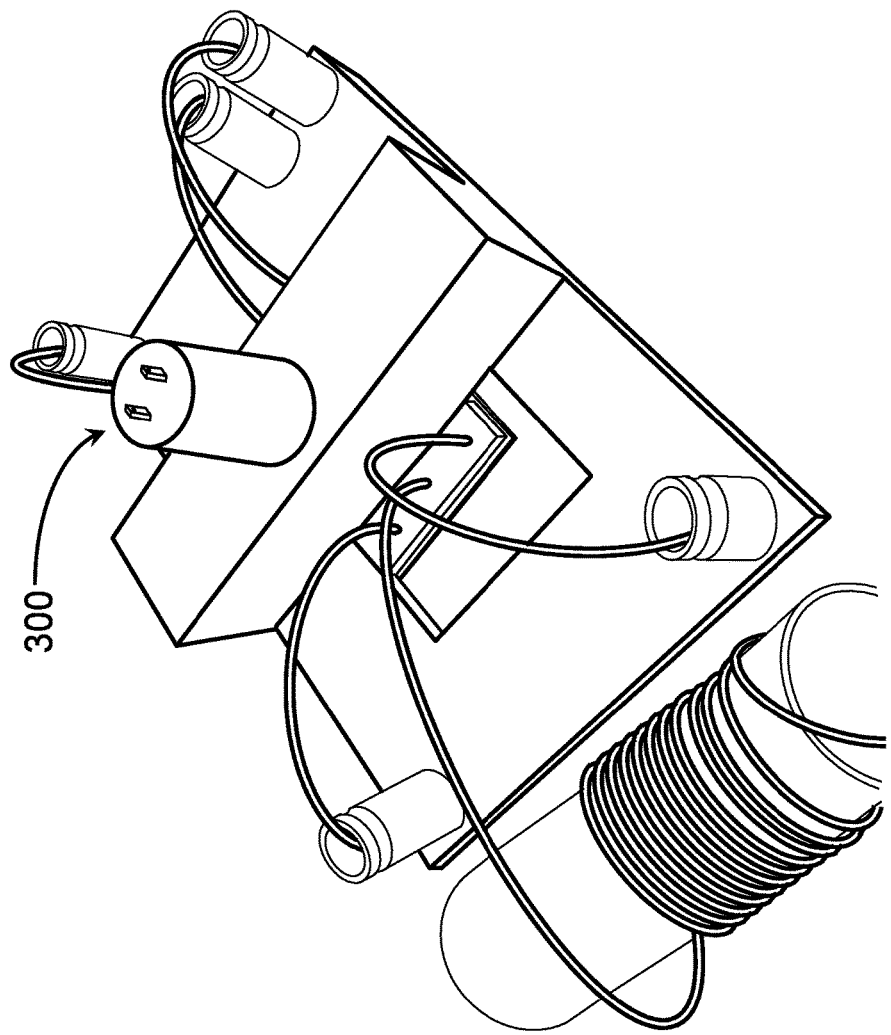
FIG. 3C shows a normally closed valve assembly according to one embodiment of the invention.

FIG. 3A shows the plastic bearing cage 320 attached to the PDMS microfluidic channels 340 that prevent the glass balls 330 from rotating when the shaft rotates. FIG. 3B shows a prototype of the normally closed valve including a brass drivehead 310 with a teardrop-shaped groove 313 that allows the balls 330 above four of the channels 340 to remain compressed by the four balls 330 that are pressed into the polymer 350, while a single channel remains uncompressed because the ball above it rises into the teardrop-shaped groove. This prevents fluid flow through the four closed channels and allows selectable fluid flow from the desired channel. The teardrop-shaped groove is sloped to recompress the glass ball when the drivehead rotates to the next position. FIG. 3C is a prototype of the normally closed five-port valve with selected colors output from the device.

Figure 4A:
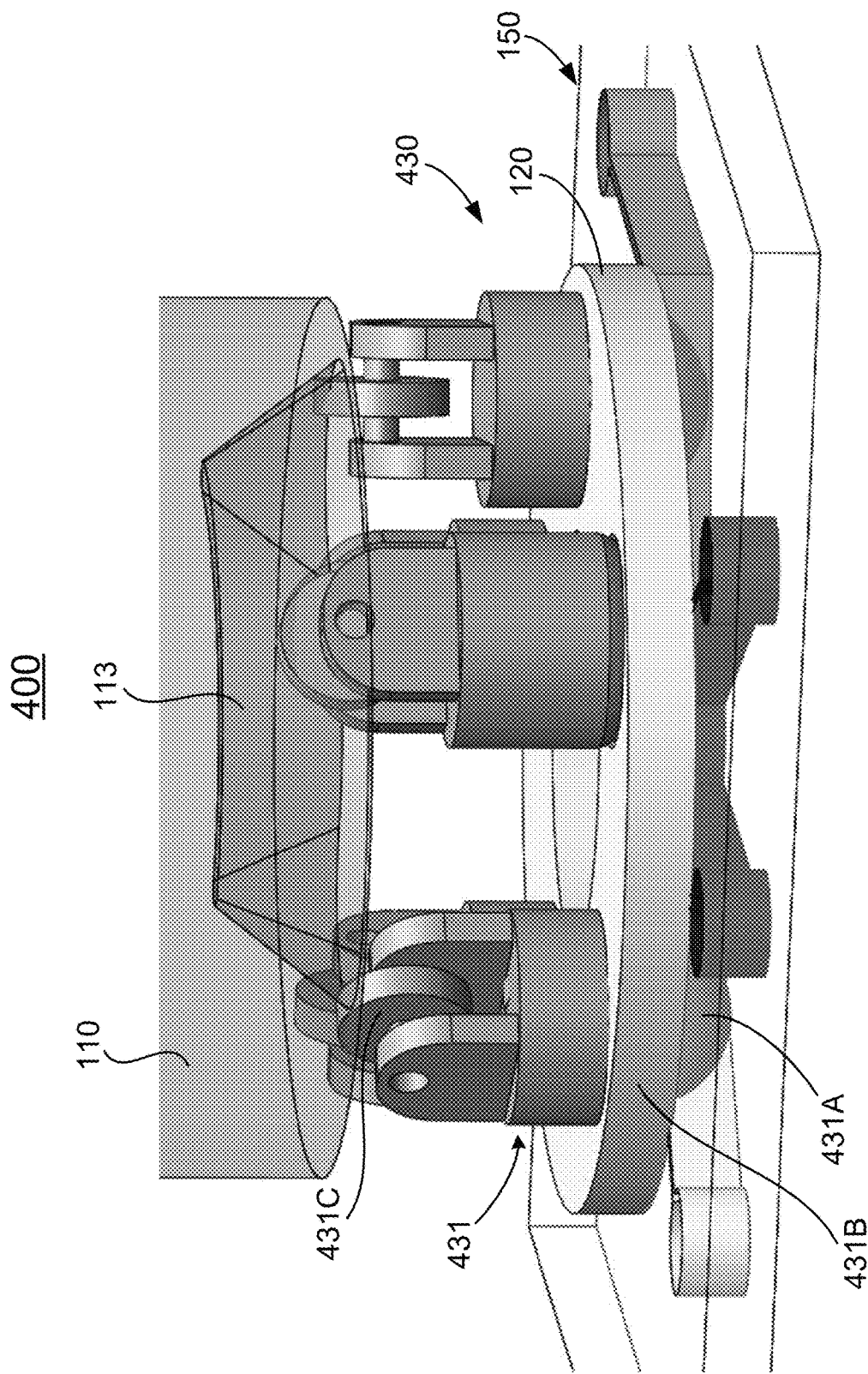
FIGS. 4A and 4B show schematically a normally closed valve according to one embodiment of the invention with rollers on each of the normally closed actuators.
Figure 4B:
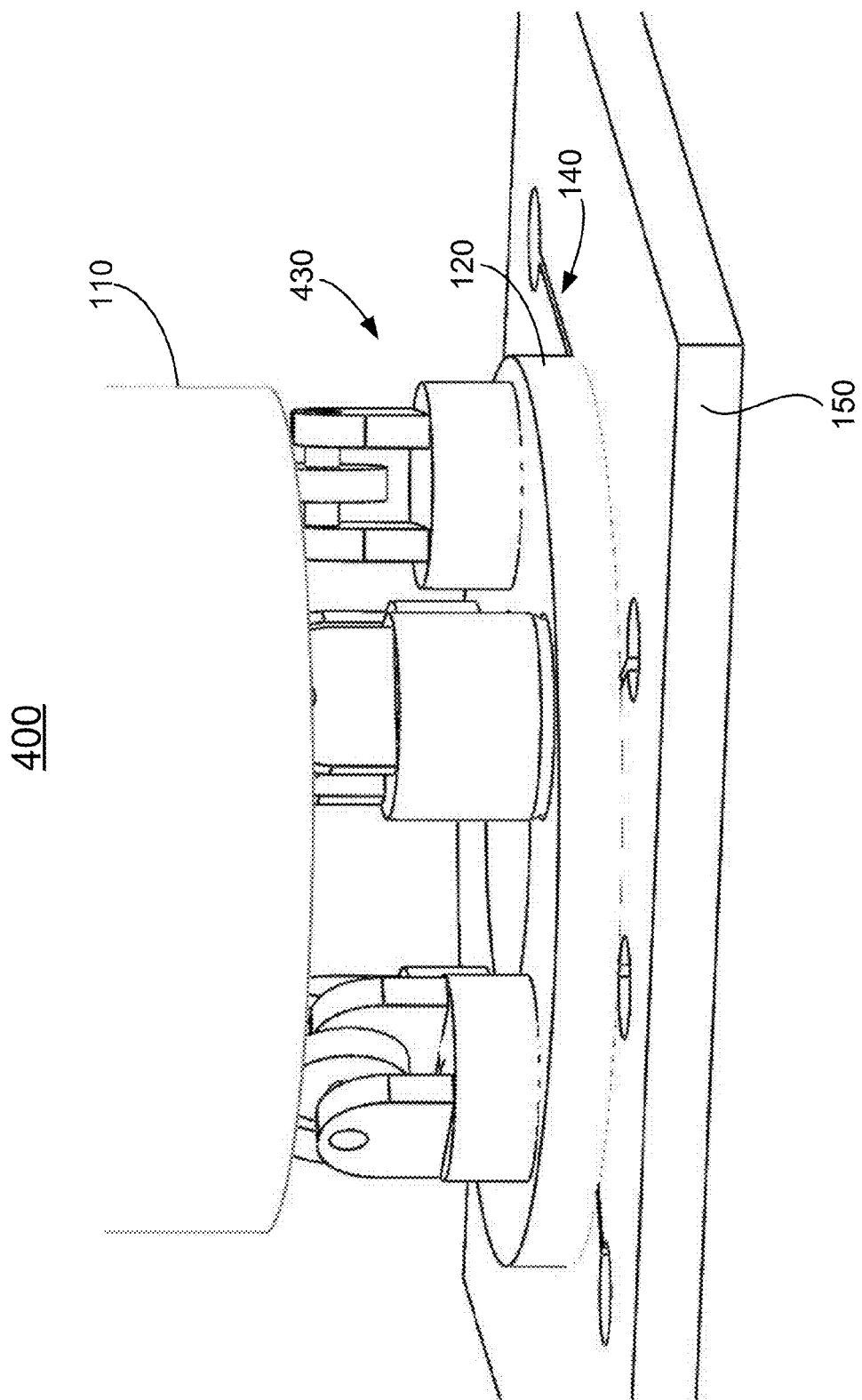

FIG. 4 shows another embodiment of the normally closed valve 400 according to the invention. The normally closed valve 400 is similar to the normally closed valve 100 shown in FIG. 1, except that each pop-up member 431 comprises a head portion 431A, a body 431B extending from the head portion 413A, and a rolling member 431C attached to the body 431A, such that as assembled, the head portion 431A is proximal to a respective fluid channel and the rolling member 431C is rotatably engaged with the drivehead 110. The operations of the normally closed valve 400 are also similar to those of the normally closed valve 100 as shown in FIG. 2. By rotating the drivehead 110 at a predetermined rotation angle, a channel can be selectively in the completely opened state, the completely closed state, or the partially opened or closed state.

Figure 5A:
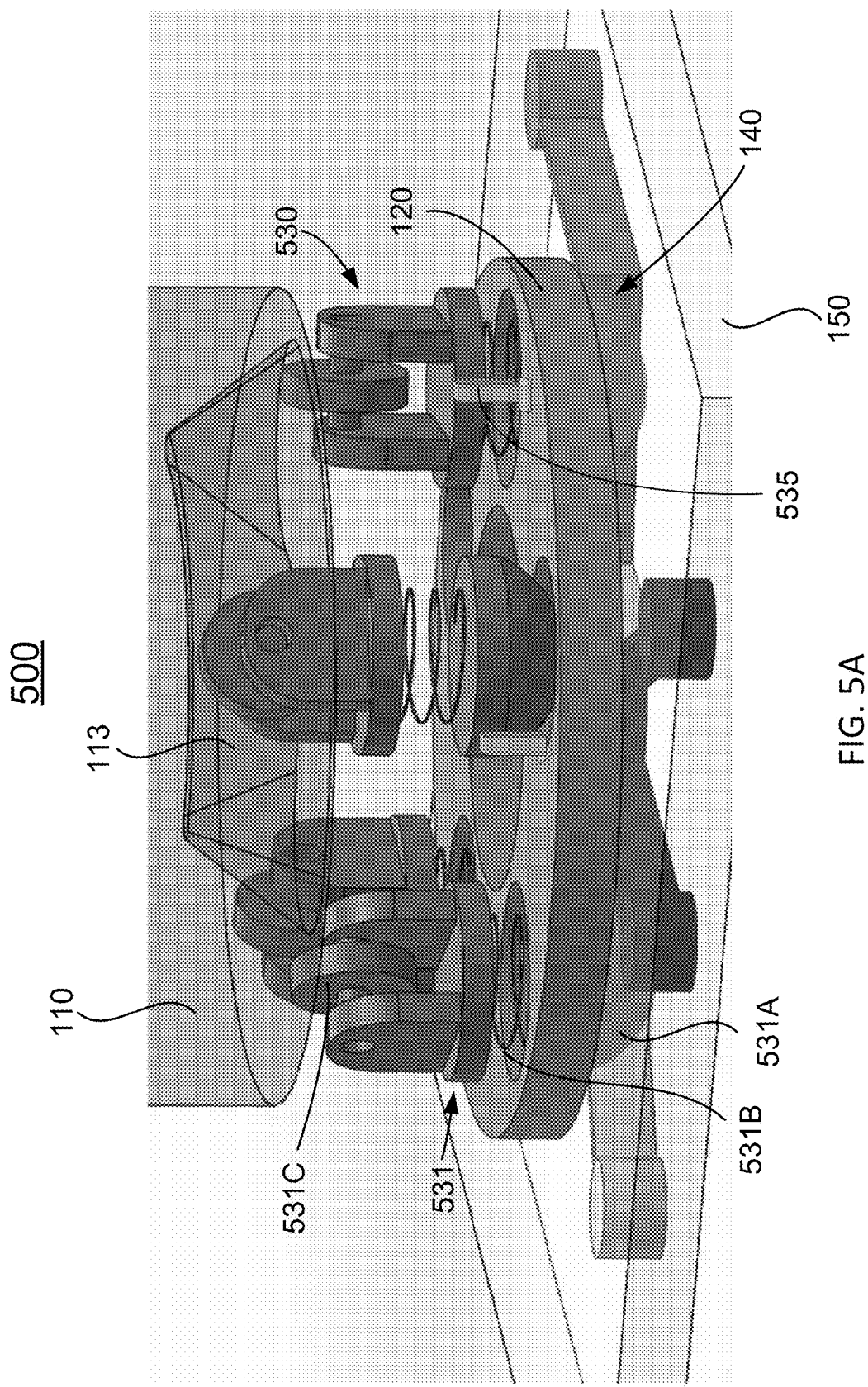
FIGS. 5A and 5B show schematically a normally closed valve according to another embodiment of the invention with self-compressing actuators with rollers.
Figure 5B:
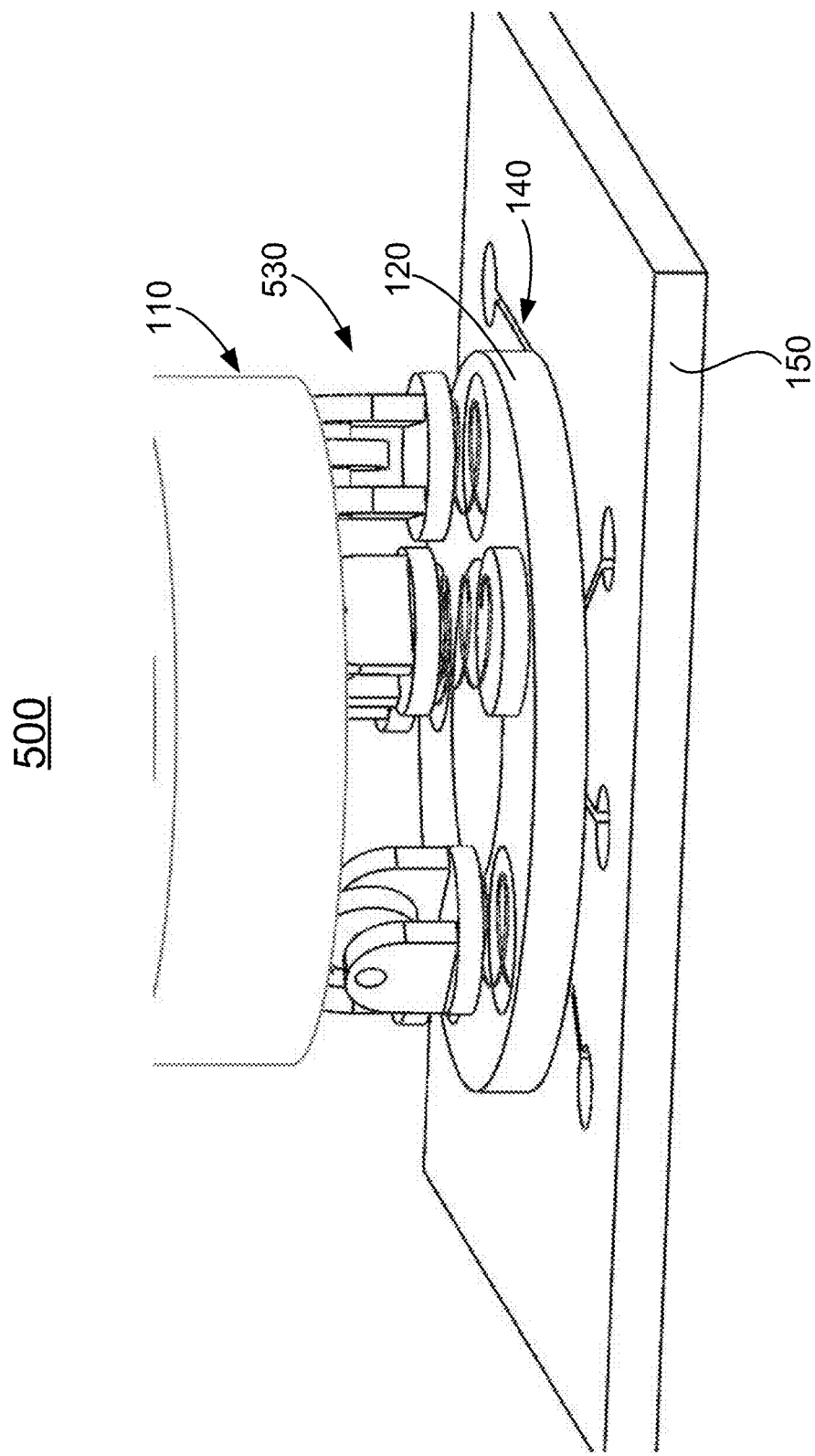
Figure 6A:
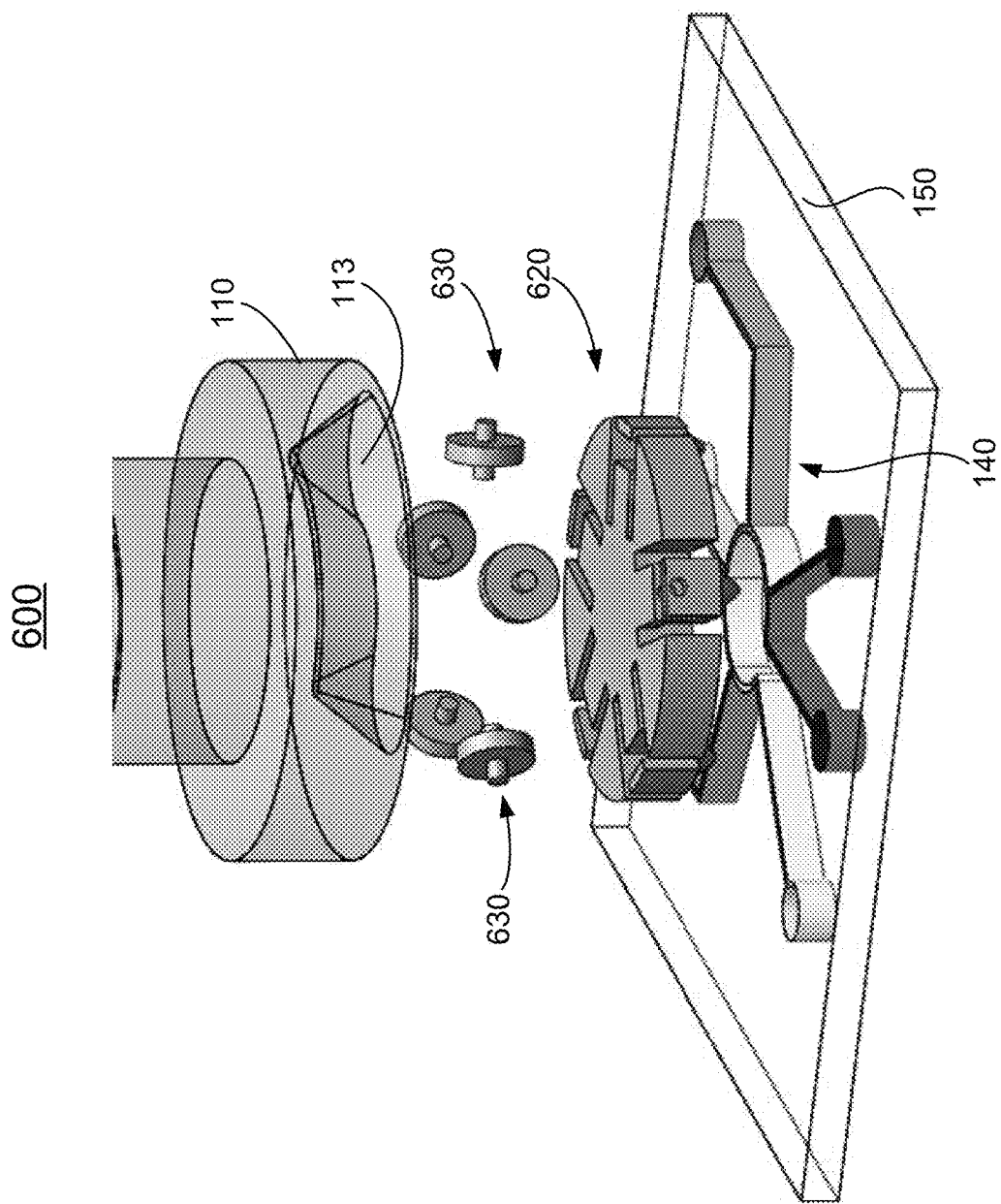
FIGS. 6A-6D show schematically a normally closed valve according to another embodiment of the invention comprising of a single piece normally closed actuator.
Figure 6B:
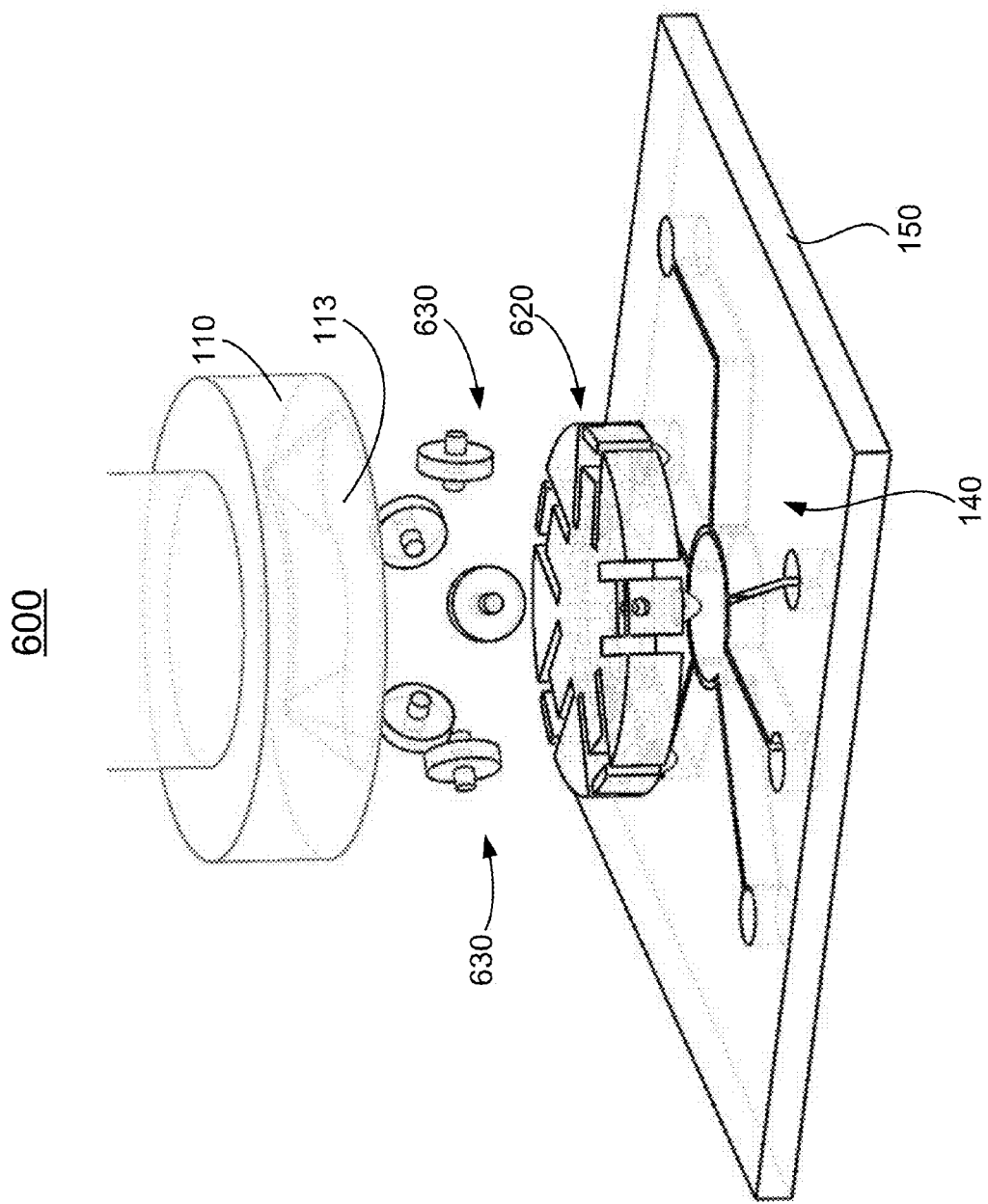
Figure 6C:
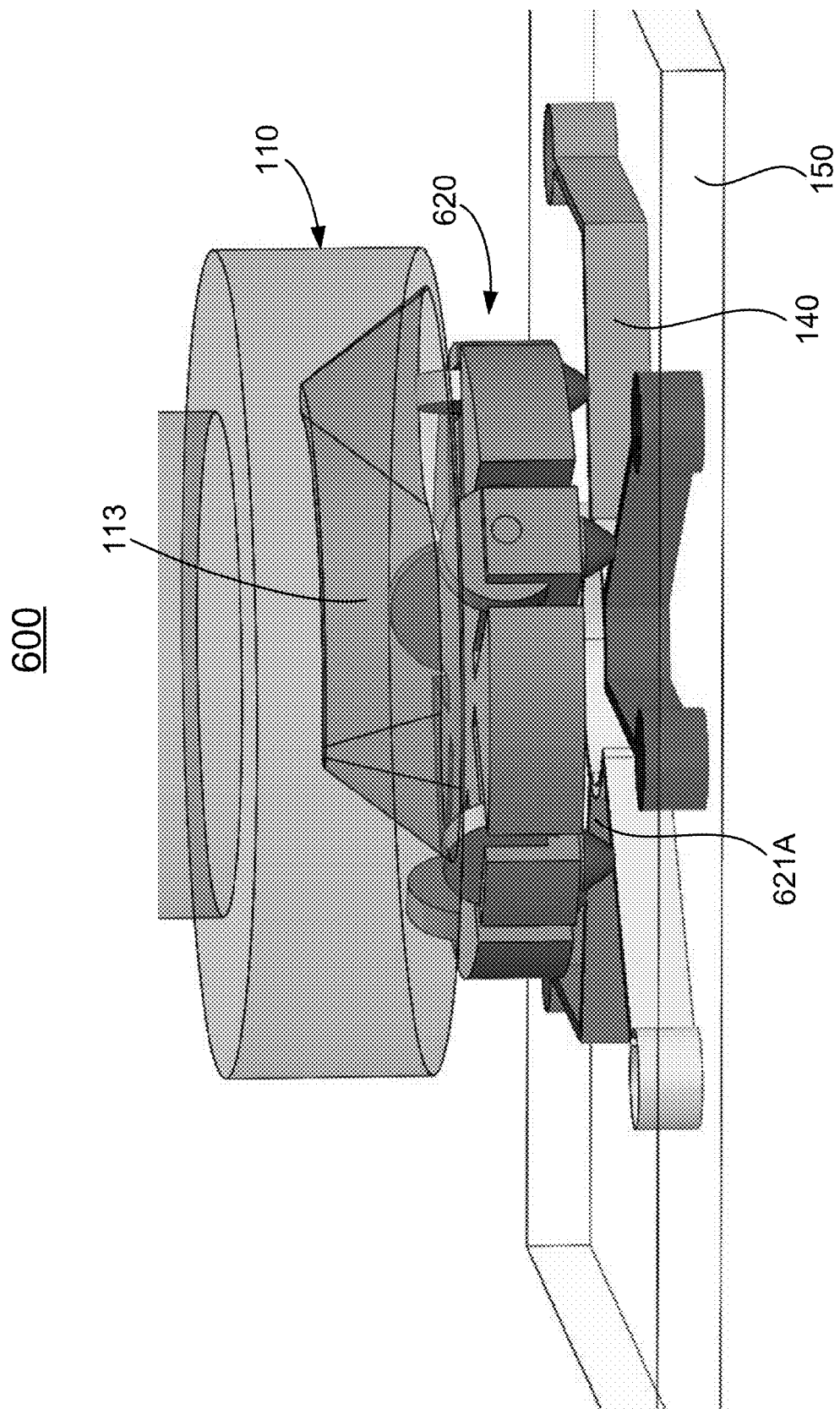
Figure 6D:
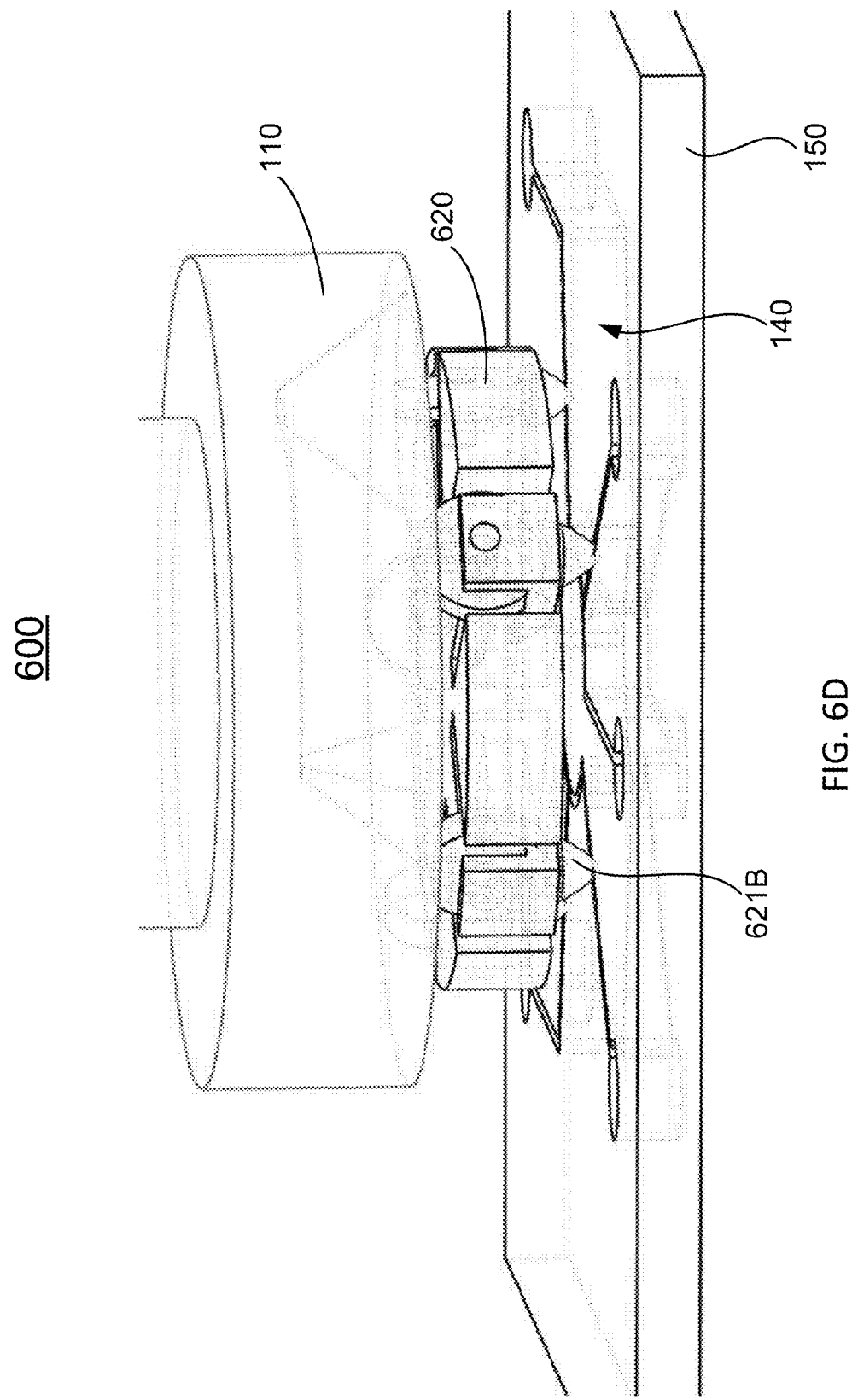
Figure 6E:
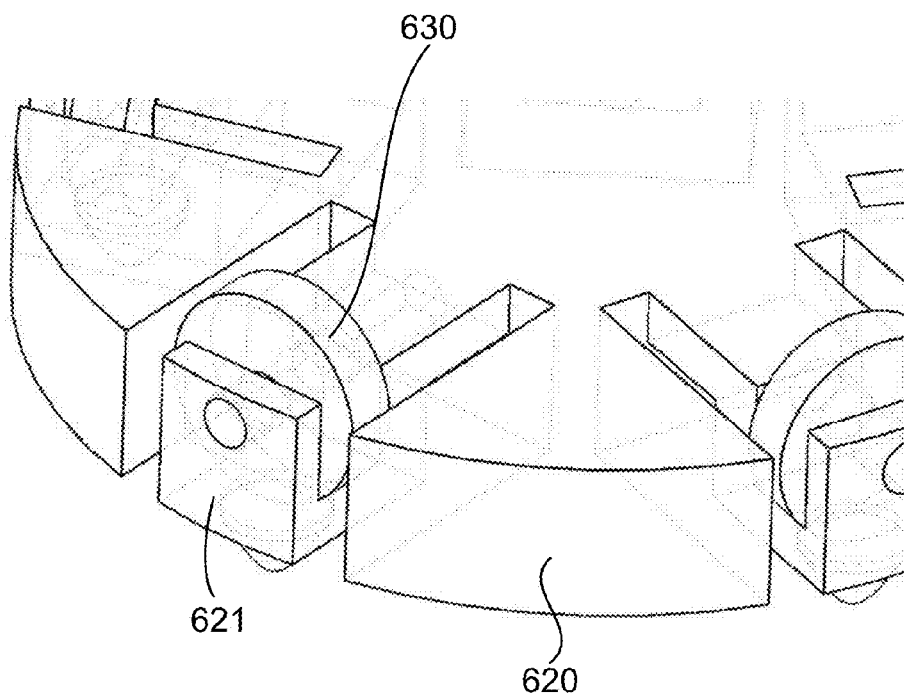
FIGS. 6E-6G show schematically partial views of the normally closed valve as shown in FIGS. 6A-6D.
Figure 6F:
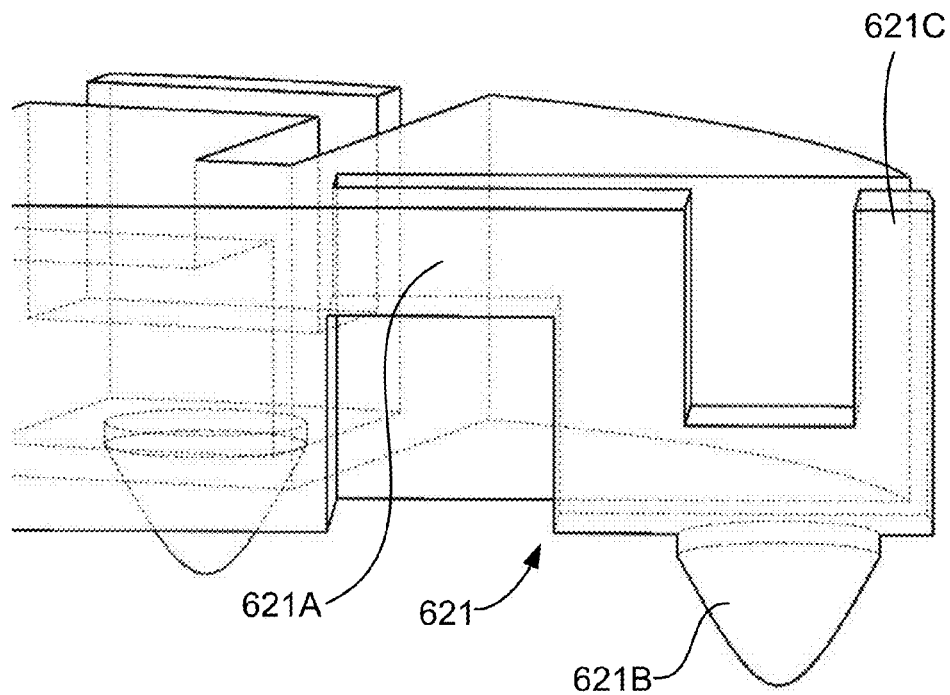
Figure 6G:
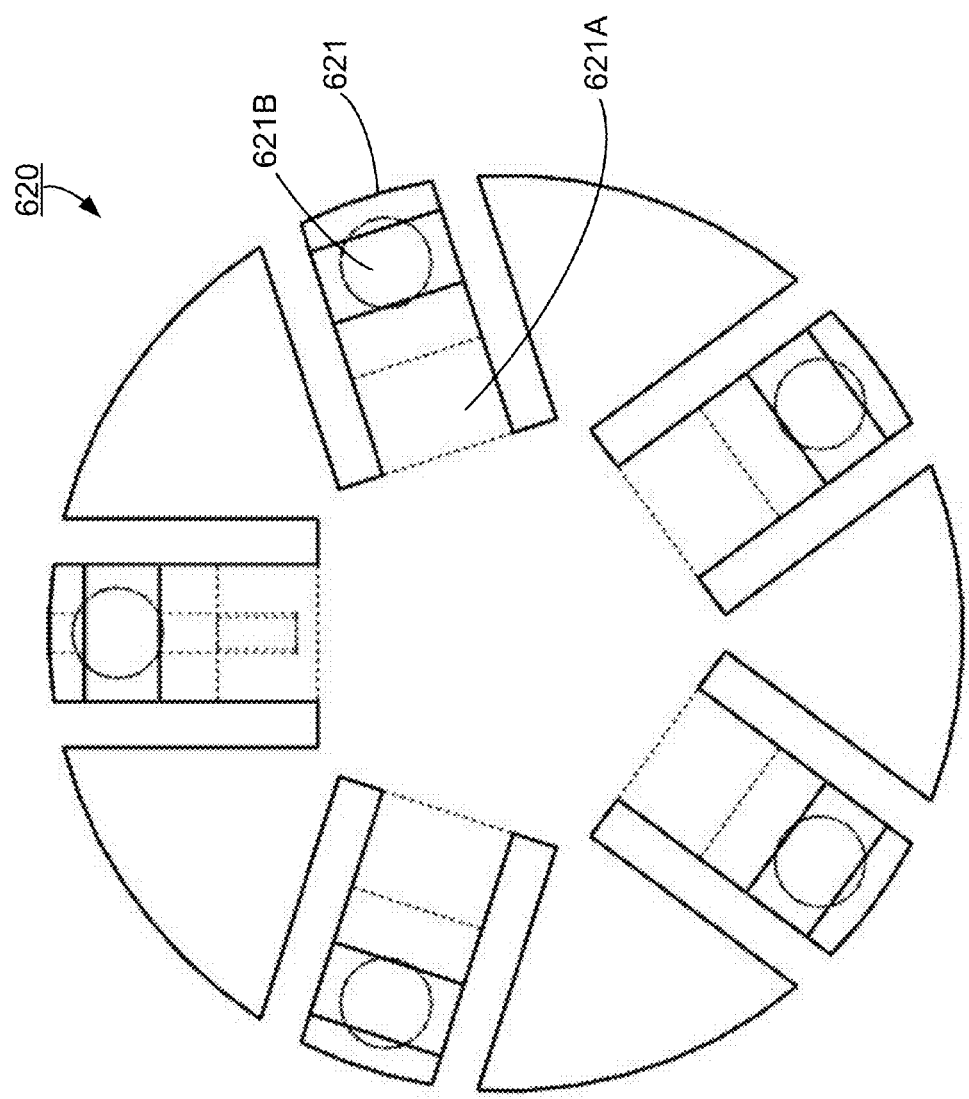

FIG. 5 shows yet another embodiment of the normally closed valve 500 according to the invention. The normally closed valve 500 is similar to the normally closed valve 400 shown in FIG. 4, except that each pop-up member 531 comprises a head portion 531A, an integrated spring 531B (or Belleville washer), and a roller 531C attached to the spring 531B. The integrated springs or Belleville washers are used to absorb shock while opening or closing the actuator and to provide a controlled compressive force when operating in the closed position. Additionally, each pop-up member 531 further comprises an alignment mechanism 535 for maintaining alignment of the roller member. The rolling member can be a ball, a roller, a wheel, or the like.

In addition, each pop-up member may be coated with a wear-resistant or lubricating film.

FIG. 6 shows an alternative embodiment of the normally closed valve 500 according to the invention. Similarly, the normally closed valve 600 has the fluid channels 140 formed in the flexible base 150, a drivehead 110 having a teardrop-shaped groove 113 formed therein, and a single piece actuator 620.

As shown in FIGS. 6A-6G, the single piece actuator 620 includes a plurality of resilient structures 621, operably placed on the flexible base 150 to position each resilient structure 621 immediately above a respective fluid channel 140. Each resilient structure 621 comprises a cantilever 621A radially extending from a central portion of the actuator 620, and a roller 630 attached to the cantilever 621A at an end portion 621C. The cantilever 621A has a head portion 621B adapted operably to press or unpress the flexible base 150 and the roller 430 is rotatably engaged with the drivehead 110. As such, when the head portion 621B of the cantilever 621A is pressed into the flexible base 150, a fluid channel that is immediately beneath the head portion 621B is compressed. Otherwise, the fluid channel is uncompressed. As the drivehead 110 rotates, any selected roller 630 is unpressed when the at least one recess arrives and pressed as the at least one recess departs, thereby selectively unoccluding or occluding a fluid flow through a desired fluid channel. In typical operation, the compression bump 621B is pushed down to compress the underlying channel except when the roller is beneath the teardrop-shaped groove 113 and the compression bump is uncompressed.

In one embodiment, the resilient structure is formed of an elastic material that is the same as or a different material from that of the flexible base.

Figure 7C:
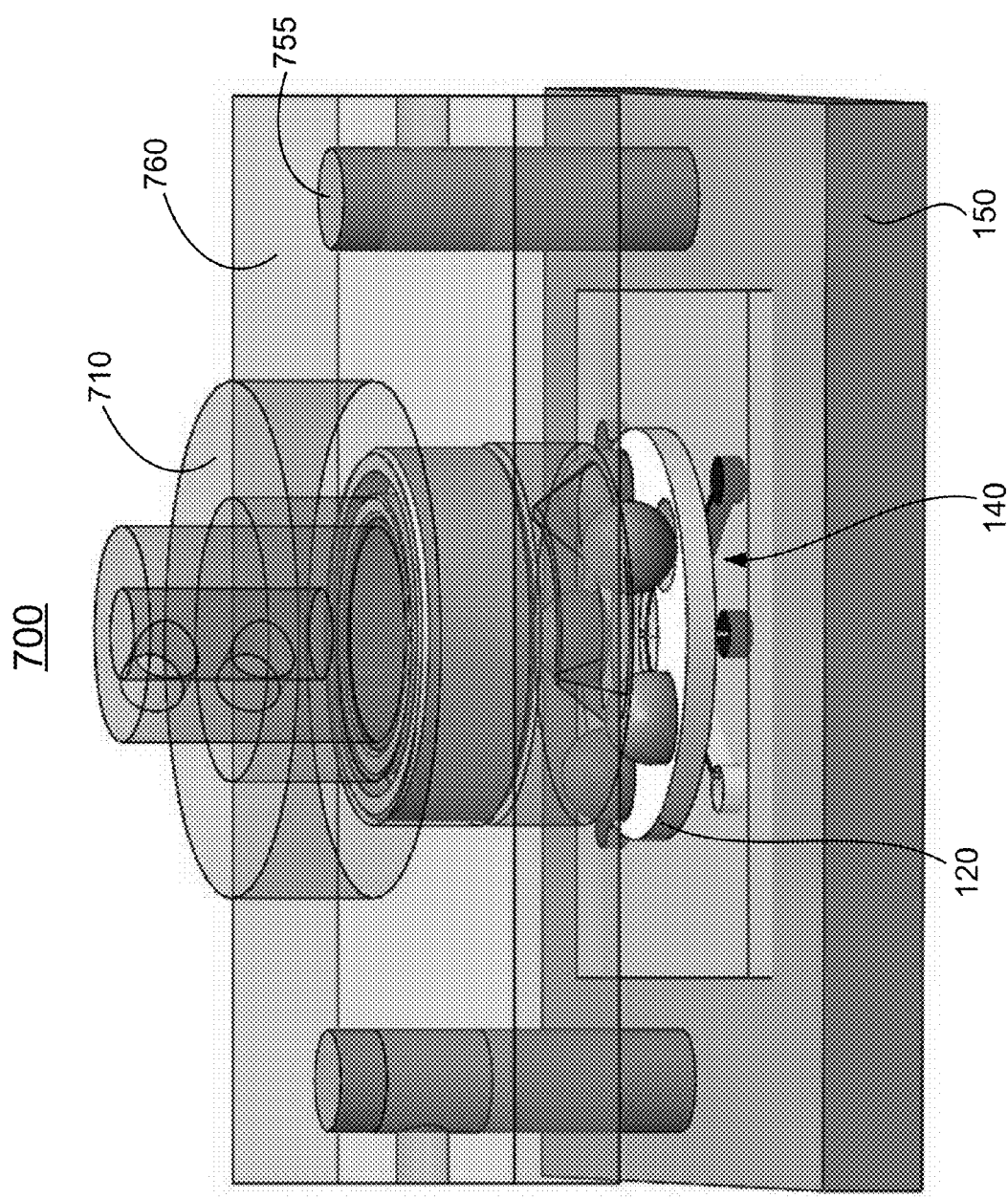
Figure 7D:
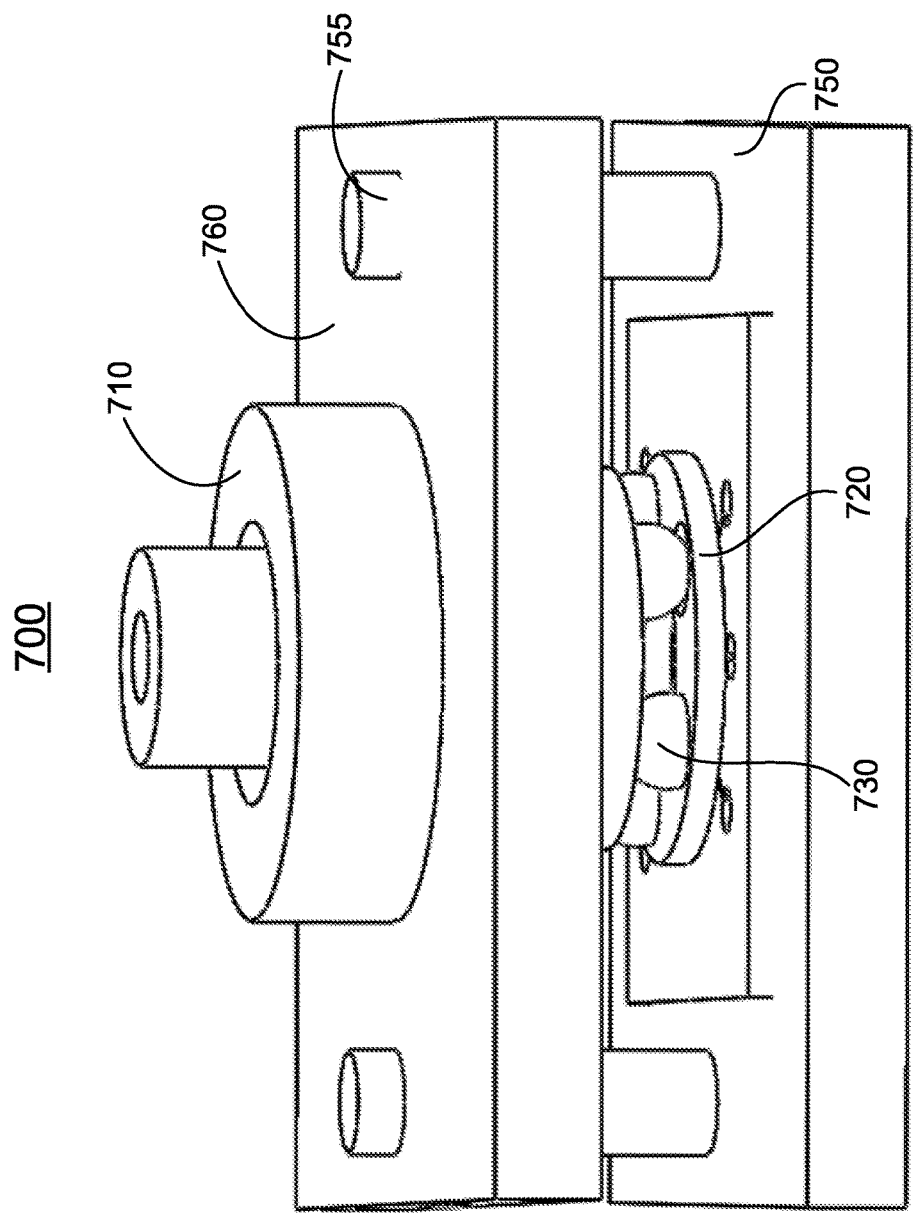

FIG. 7 shows an alternative configuration of a normally closed valve 700 for providing compression. This configuration requires a bearing for alignment and to allow the inner shaft to rotate and does not require the bearings in the motor to provide the requisite compressive force.

Specifically, the normally closed valve 700 has the fluid channels 140 formed in the flexible base 150, the drivehead 110 having a teardrop-shaped groove 113 formed therein, and the actuator 120, which are the same as that of the normally closed valve 100 shown in FIG. 1. As shown in FIG. 1, the drivehead 110 has a first cylindrical portion on which the teardrop-shaped groove is formed, and a second cylindrical portion extending coaxially from the first cylindrical portion, where the first cylindrical portion has a diameter that is greater than that of the second cylindrical portion. The second cylindrical portion is engaged with a motor.

Further, the normally closed valve 700 includes a bearing 718 rotatably attached onto the second cylindrical portion of the drivehead 110, and a tension holding plate 760 having an opening 762 formed to accommodate the bearing 718 that is adjustably mounted to alignment pins 755 for transferring tensioning pressure via the bearing 718 to the fluidic channels 140 thereunder. The alignment pins 755 are vertically positioned in relation to the flexible base 150 such that each ball bearing of the actuator is aligned with the respective fluid channel thereunder and the drivehead 110 is rotatably engaged with the actuator.

Figure 8A:
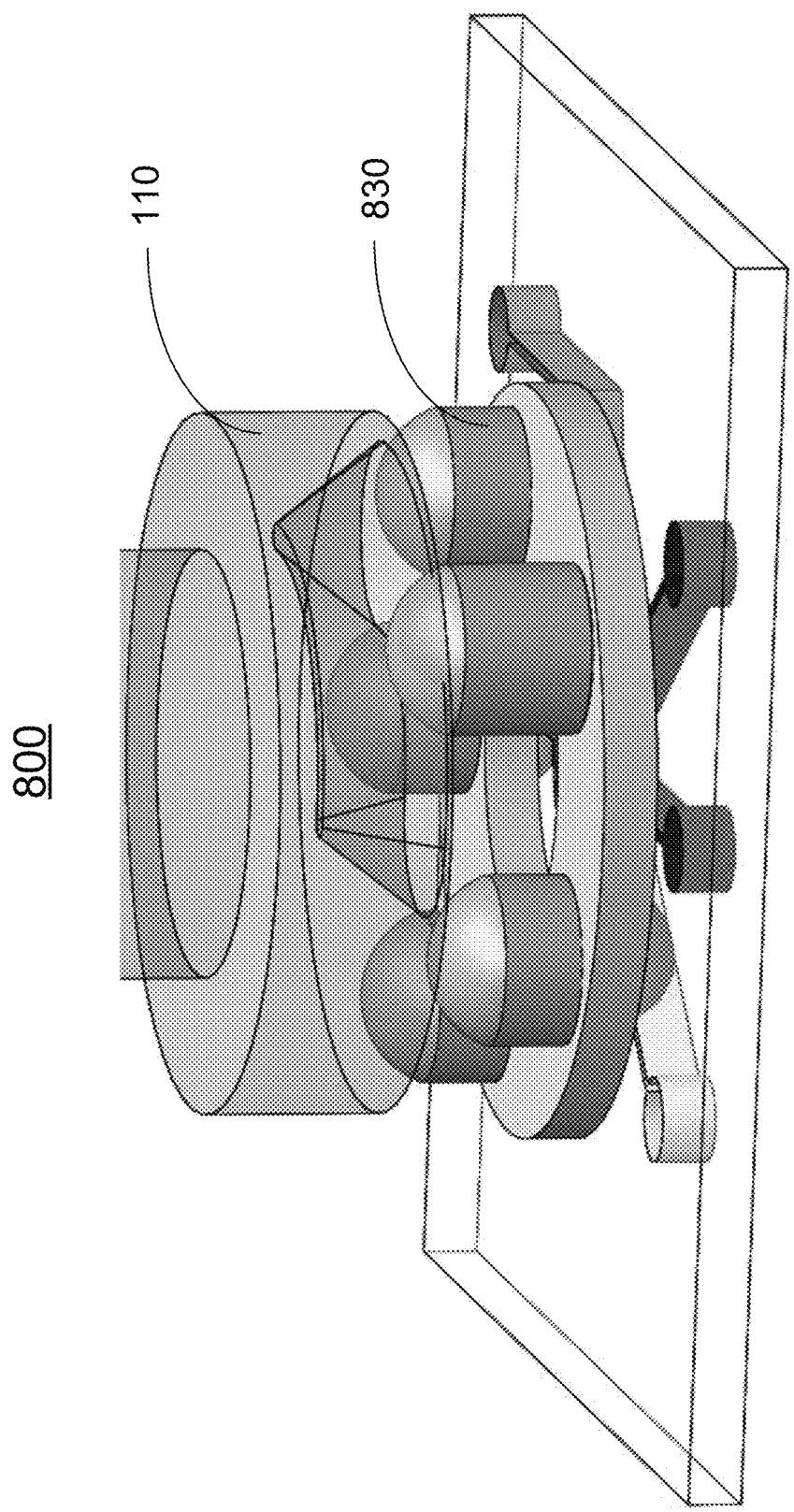

FIG. 8 shows an alternative configuration of the normally closed valve 800. The normally closed valve 800 is similar to the normally closed valve 100 shown in FIG. 1, except that each pop-up member is an actuating pin 830, or a cylinder whose end portions have convex curved surfaces, in this embodiment of the design.

Figure 9A:
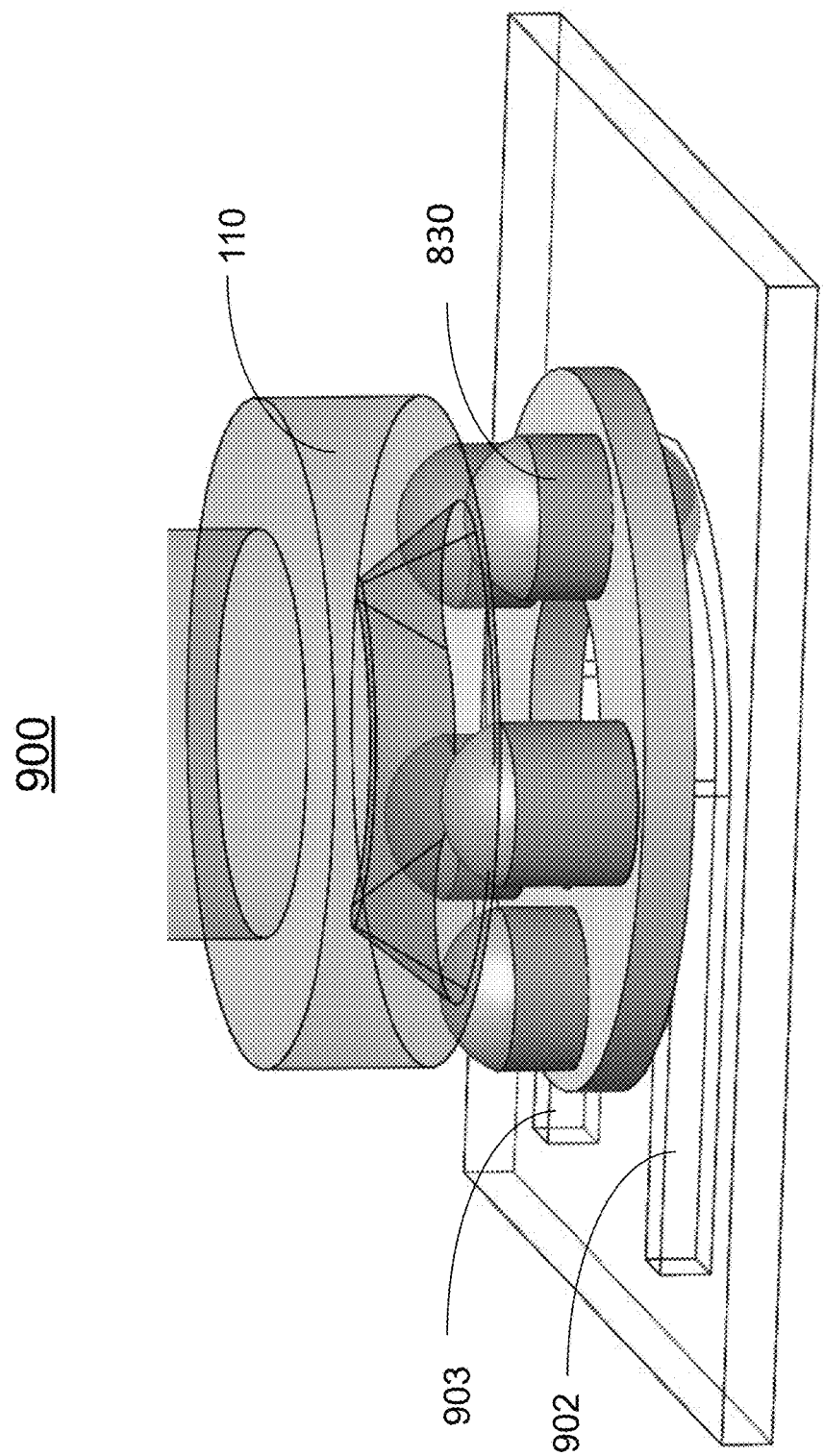
FIGS. 9A-9C show schematically the fluidic channels arranged as a pump in one embodiment of the invention.
Figure 9B:
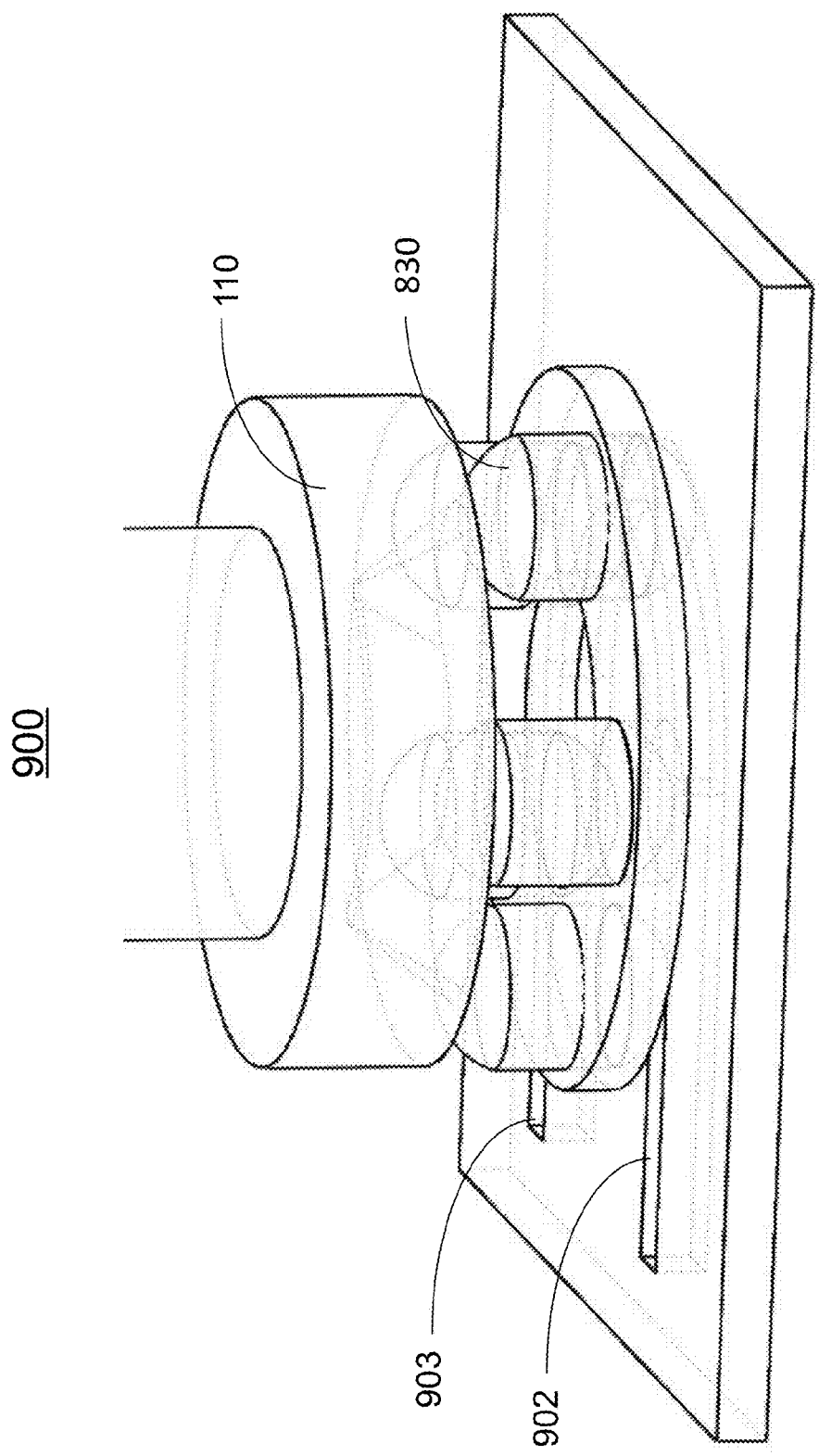
Figure 9C:
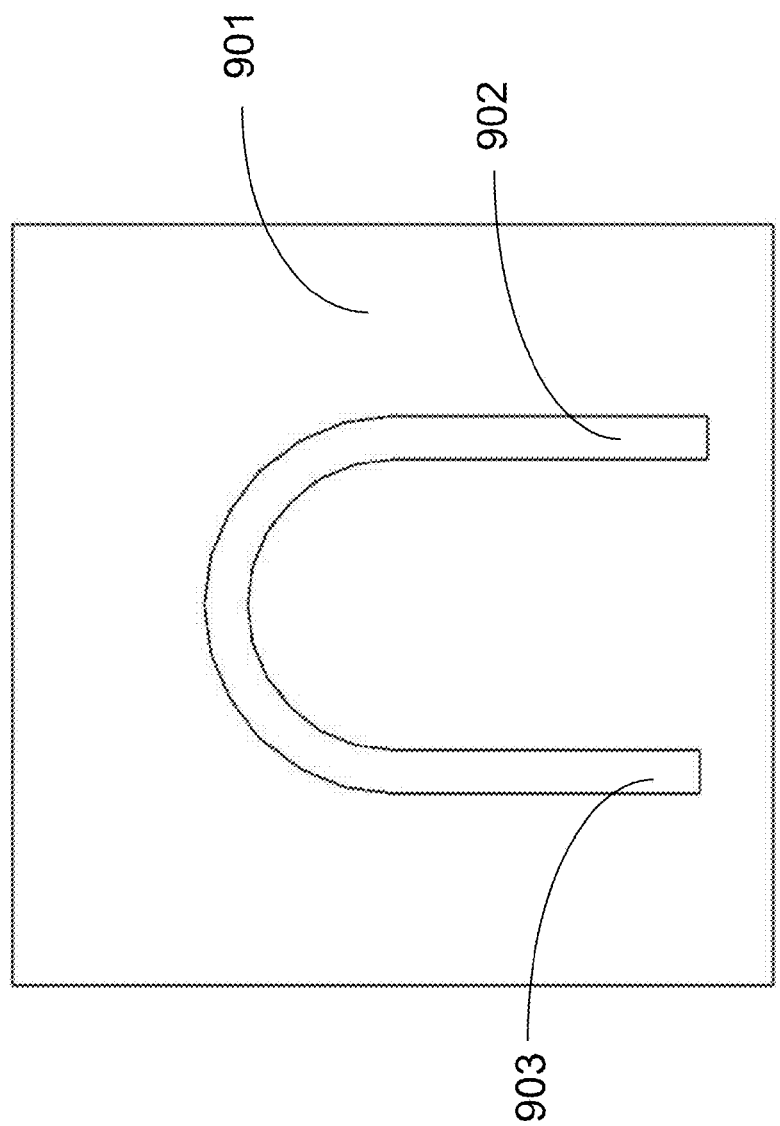

FIG. 9 shows an embodiment of the fluidic base membrane such that the drivehead and pop-up members are configured to serve as a pump. Flexible base layer 901 has embedded channels with an inlet port 902 and outlet port 903. As the drivehead 110 rotates counterclockwise, the actuating pins 830 open and close to produce fluid flow.

FIG. 10 shows schematically a drivehead utilized in a valve or pump according to one embodiment of the invention. In this exemplary embodiment, the drivehead has three circular concentric variable-depth grooves 1011, 1012 and 1013 recessed from the front surface of the drivehead 1010, or, alternatively, multiple variable-depth ridges. The multiple grooves or ridges are located along multiple concentric rings surrounding the rotational axis of the drivehead 1010. As such, in operation, the rolling members are actuated by these circular concentric variable-depth grooves or, alternatively, variable-depth ridges as to provide varying degrees of actuation of the pop-up members as a function of the rotation angle of the drivehead. The number and positioning of the variable height or depth regions of the concentric grooves or concentric ridges can be arranged in such a way that when the drivehead is rotated to certain specific rotational angles, some combination of the multiple fluidic channels can be fully occluded, partially occluded, or fully un-occluded.

In one aspect, the invention relates to a system or modules comprising one or more normally closed valves as disclosed above. The system or module includes, but is not limited to, a Perfusion Controller, a MicroClinical Analyzer, and/or a Microformulator.

In another aspect of the invention, a method for selectively occluding or unoccluding a fluid flow through a desired fluid channel includes providing a plurality of fluid channels in fluid communication with each other, wherein the plurality of fluid channels is defined in a flexible base and configured such that when a fluid channel is compressed, a fluid flow through the fluid channel is occluded, otherwise, the fluid flow through the fluid channel is unoccluded; and selectively compressing or uncompressing the desired fluid channel.

In one embodiment, the step of selectively compressing or uncompressing the desired fluid channel is performed with an actuator driven by a drivehead having a surface and at least one recess formed on the surface as disclosed above.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A normally closed valve, comprising:
   (a) a plurality of fluid channels in fluid communication with each other, defined in a flexible base such that when a fluid channel is compressed, a fluid flow through the fluid channel is occluded, otherwise, the fluid flow through the fluid channel is unoccluded;
   (b) an actuator comprising a cage defining a plurality of spaced-apart openings, and a plurality of pop-up members, each pop-up member retained in a respective opening of the cage and being vertically movable therein, wherein the actuator is placed on the flexible base to constrain each pop-up member in a position immediately above a respective fluid channel, such that when a pop-up member is pressed into the flexible base, a fluid channel that is immediately beneath the pop-up member is compressed, otherwise, the fluid channel is uncompressed; and
   (c) a drivehead having a surface and at least one recess formed on the surface, wherein the drivehead is rotatably engaged with the actuator such that each pop-up member is pressed into the flexible base normally, and as the drivehead rotates, any selected pop-up member is unpressed or partially unpressed when the at least one recess arrives and pressed as the at least one recess departs, thereby selectively unoccluding or occluding a fluid flow through a desired fluid channel.

2. The normally closed valve of claim 1, wherein the at least one recess comprises at least one teardrop-shaped groove located along single or multiple concentric rings surrounding a rotational axis of the drivehead.

3. The normally closed valve of claim 2, wherein the at least one teardrop-shaped groove has sloped sidewalls with fixed or variable taper-rates such that when the drivehead rotates at predetermined rotation angles, the at least one teardrop-shaped groove positions over a pop-up member so as to partially unocclude or completely unocclude its underlying channel, and at other rotation angles, the at least one teardrop-shaped groove is displaced from the pop-up member so as to completely occlude its underlying channel.

4. The normally closed valve of claim 1, wherein the drivehead is driven by a motor.

5. The normally closed valve of claim 4, wherein the drivehead has a first cylindrical portion on which the recess is formed, and a second cylindrical portion extending coaxially from the first cylindrical portion, wherein the first cylindrical portion has a diameter that is greater than that of the second cylindrical portion, and wherein the second cylindrical portion is engaged with the motor.

6. The normally closed valve of claim 5, further comprising:
   (a) a bearing rotatably attached onto the second cylindrical portion of the drivehead; and
   (b) a tension holding plate having an opening formed to accommodate the bearing, adjustably mounted to alignment pins for transferring tensioning pressure via the bearing to the fluidic channels thereunder, wherein the alignment pins are vertically positioned in relation to the flexible base such that each pop-up member of the actuator is aligned with the respective fluid channel thereunder and the drivehead is rotatably engaged with the actuator.

7. The normally closed valve of claim 1, wherein each of the plurality of pop-up members comprises a ball.

8. The normally closed valve of claim 1, wherein each of the plurality of pop-up members comprises a head portion, a body extending from the head portion, and a rolling member attached to the body, such that as assembled, the head portion is proximal to a respective fluid channel and the rolling member is rotatably engaged with the drivehead.

9. The normally closed valve of claim 8, wherein each of the plurality of pop-up members further comprises an alignment mechanism for maintaining alignment of the roller member.

10. The normally closed valve of claim 8, wherein the rolling member comprises a ball, roller, or a wheel.

11. The normally closed valve of claim 8, wherein the body comprises a spring or Belleville washer.

12. The normally closed valve of claim 1, wherein each of the plurality of pop-up members comprises a cylinder whose end portions have convex curved surfaces, such that as assembled, one end portion is proximal to a respective fluid channel and the other end portion is engaged with the drivehead.

13. The normally closed valve of claim 1, wherein each of the plurality of pop-up members is coated with a wear-resistant or lubricating film.

14. The normally closed valve of claim 1, wherein the flexible base is formed of an elastic material.

15. The normally closed valve of claim 1, wherein the elastic material includes polydimethylsiloxane (PDMS).

16. The normally closed valve of claim 1, further comprising at least one offset fluid channel in fluid communication with the plurality of fluid channels, formed in the flexible base and offset from the plurality of pop-up members of the actuator.

17. A system comprising one or more normally closed valves, each normally closed valve recited in claim 1.

18. A normally closed valve, comprising:
   (a) a plurality of fluid channels in fluid communication with each other, defined in a flexible base formed of an elastic material such that when a fluid channel is compressed, a fluid flow through the fluid channel is occluded, otherwise, the fluid flow through the fluid channel is unoccluded; and (b) means for selectively compressing or uncompressing a desired fluid channel wherein the selectively compressing or uncompressing means comprises a drivehead having a surface and at least one recess formed on the surface, and wherein the at least one recess comprises at least one groove located along single or multiple concentric rings surrounding a rotational axis of the drivehead.

19. The normally closed valve of claim 18, wherein the selectively compressing or uncompressing means further comprises an actuator comprising a plurality of resilient structures, placed on the flexible base to position each resilient structure immediately above a respective fluid channel, such that when a resilient structure is pressed into the flexible base, a fluid channel that is immediately beneath the resilient structure is compressed, otherwise, the fluid channel is uncompressed, wherein the drivehead is rotatably engaged with the actuator such that each resilient structure is pressed into the flexible base normally, and as the drivehead rotates, any selected resilient structure is unpressed or partially unpressed when the at least one recess arrives and pressed as the at least one recess departs, thereby selectively unoccluding or occluding a fluid flow through a desired fluid channel.

20. The normally closed valve of claim 19, wherein each resilient structure comprises a cantilever radially extending from a central portion of the actuator, and a rolling member attached to the cantilever, wherein the cantilever has a head portion adapted to press or unpress the flexible base and the rolling member is rotatably engaged with the drivehead.

21. The normally closed valve of claim 19, wherein each resilient structure is formed of an elastic material that is the same as or a different material from that of the flexible base.

22. The normally closed valve of claim 19, further comprising at least one offset fluid channel in fluid communication with the plurality of fluid channels, formed in the flexible base and offset from the plurality of resilient structures of the actuator.

23. The normally closed valve of claim 18, wherein the selectively compressing or uncompressing means further comprises an actuator comprising a cage defining a plurality of spaced-apart openings, and a plurality of pop-up members, each pop-up member retained in a respective opening of the cage and being vertically movable therein, wherein the actuator is placed on the flexible base to constrain each pop-up member in a position immediately above a respective fluid channel, such that when a pop-up member is pressed into the flexible base, a fluid channel that is immediately beneath the pop-up member is compressed, otherwise, the fluid channel is uncompressed, wherein the drivehead is rotatably engaged with the actuator such that each pop-up member is pressed into the flexible base normally, and as the drivehead rotates, any selected pop-up member is unpressed or partially unpressed when the at least one recess arrives and pressed as the at least one recess departs, thereby selectively unoccluding or occluding a fluid flow through a desired fluid channel.

24. The normally closed valve of claim 23, wherein each of the plurality of pop-up members is coated with a wear-resistant or lubricating film.

25. The normally closed valve of claim 23, wherein each of the plurality of pop-up members comprises a ball.

26. The normally closed valve of claim 23, wherein each of the plurality of pop-up members comprises a head portion, a body extending from the head portion, and a rolling member attached to the body, such that as assembled, the head portion is proximal to a respective fluid channel and the rolling member is rotatably engaged with the drivehead.

27. The normally closed valve of claim 26, wherein each of the plurality of pop-up members further comprises an alignment mechanism for maintaining alignment of the roller member.

28. The normally closed valve of claim 26, wherein the rolling member comprises a ball, roller, or a wheel.

29. The normally closed valve of claim 26, wherein the body comprises a spring or Belleville washer.

30. The normally closed valve of claim 23, wherein each of the plurality of pop-up members comprises a cylinder whose end portions have convex curved surfaces, such that as assembled, one end portion is proximal to a respective fluid channel and the other end portion is engaged with the drivehead.

31. The normally closed valve of claim 18, wherein the at least one groove comprises at least one teardrop-shaped groove having sloped sidewalls with fixed or variable taper-rates.

32. A normally closed valve, comprising:
(a) a plurality of fluid channels in fluid communication with each other, defined in a flexible base formed of an elastic material such that when a fluid channel is compressed, a fluid flow through the fluid channel is occluded, otherwise, the fluid flow through the fluid channel is unoccluded, and
(b) means for selectively compressing or uncompressing a desired fluid channel, wherein the selectively compressing or uncompressing means comprises a drivehead having a surface and at least one recess formed on the surface, wherein the at least one recess comprises at least one circular concentric variable-depth groove, or variable-depth ridge attached to the drivehead in such a manner as to provide varying degrees of actuation of pop-up members as a function of the rotation angle of the drivehead, and wherein the number and positioning of the variable height or depth regions of the concentric grooves or concentric ridges are arranged in such a way that when the drivehead is rotated to certain predetermined rotational angles, the fluidic channels are selectively fully occluded, partially occluded, or fully un-occluded.

33. The normally closed valve of claim 18, wherein the drivehead is driven by a motor.

34. The normally closed valve of claim 33, wherein the drivehead has a first cylindrical portion on which the recess is formed, and a second cylindrical portion extending coaxially from the first cylindrical portion, wherein the first cylindrical portion has a diameter that is greater than that of the second cylindrical portion, and wherein the second cylindrical portion is engaged with the motor.

35. The normally closed valve of claim 34, further comprising:
(a) a bearing rotatably attached onto the second cylindrical portion of the drivehead; and
(b) a tension holding plate having an opening formed to accommodate the bearing, adjustably mounted to alignment pins for transferring tensioning pressure via the bearing to the fluidic channels thereunder, wherein the alignment pins are vertically positioned in relation to the flexible base such that each pop-up member of the actuator is aligned with the respective fluid channel thereunder and the drivehead is rotatably engaged with the actuator.

36. The normally closed valve of claim 23, further comprising at least one offset fluid channel in fluid communication with the plurality of fluid channels, formed in the flexible base and offset from the plurality of pop-up members of the actuator.

37. A system comprising one or more normally closed valves, each normally closed valve recited in claim 18.

38. A method for selectively occluding or unoccluding a fluid flow through a desired fluid channel, comprising:
(a) providing a plurality of fluid channels in fluid communication with each other, wherein the plurality of fluid channels is defined in a flexible base and configured such that when a fluid channel is compressed, a fluid flow through the fluid channel is completely occluded or partially occluded, otherwise, the fluid flow through the fluid channel is unoccluded; and
(b) selectively compressing or uncompressing the desired fluid channel, wherein the step of selectively compressing or uncompressing the desired fluid channel is performed with an actuator driven by a drivehead having a surface and at least one recess formed on the surface, and wherein the at least one recess comprises at least one groove located along single or multiple concentric rings surrounding a rotational axis of the drivehead.

39. The method of claim 38, wherein the fluidic channels beneath the actuator are arranged in a way to serve as a pump, with the actuator above opening and closing in a controlled fashion to produce fluid flow.

40. The method of claim 38, wherein the actuator comprises a plurality of resilient structures, placed on the flexible base to position each resilient structure immediately above a respective fluid channel, such that when a resilient structure is pressed into the flexible base, a fluid channel that is immediately beneath the resilient structure is compressed, otherwise, the fluid channel is uncompressed, and wherein the drivehead is rotatably engaged with the actuator such that each resilient structure is pressed into the flexible base normally, and as the drivehead rotates, any selected resilient structure is unpressed or partially unpressed when the at least one recess arrives and pressed as the at least one recess departs, thereby selectively unoccluding or occluding a fluid flow through the desired fluid channel.

41. The method of claim 38, wherein the actuator comprises a cage defining a plurality of spaced-apart openings, and a plurality of pop-up members, each pop-up member retained in a respective opening of the cage and being vertically movable therein, wherein the actuator is placed on the flexible base to constrain each pop-up member in a position immediately above a respective fluid channel, such that when a pop-up member is pressed into the flexible base, a fluid channel that is immediately beneath the pop-up member is compressed, otherwise, the fluid channel is uncompressed, wherein the drivehead is rotatably engaged with the actuator such that each pop-up member is pressed into the flexible base normally, and as the drivehead rotates, any selected pop-up member is unpressed or partially unpressed when the at least one recess arrives and pressed as the at least one recess departs, thereby selectively unoccluding or occluding a fluid flow through the desired fluid channel.

42. The method of claim 38, wherein the at least one groove comprises at least one teardrop-shaped groove having sloped sidewalls with fixed or variable taper-rates.

* * * * *